Figure 1:
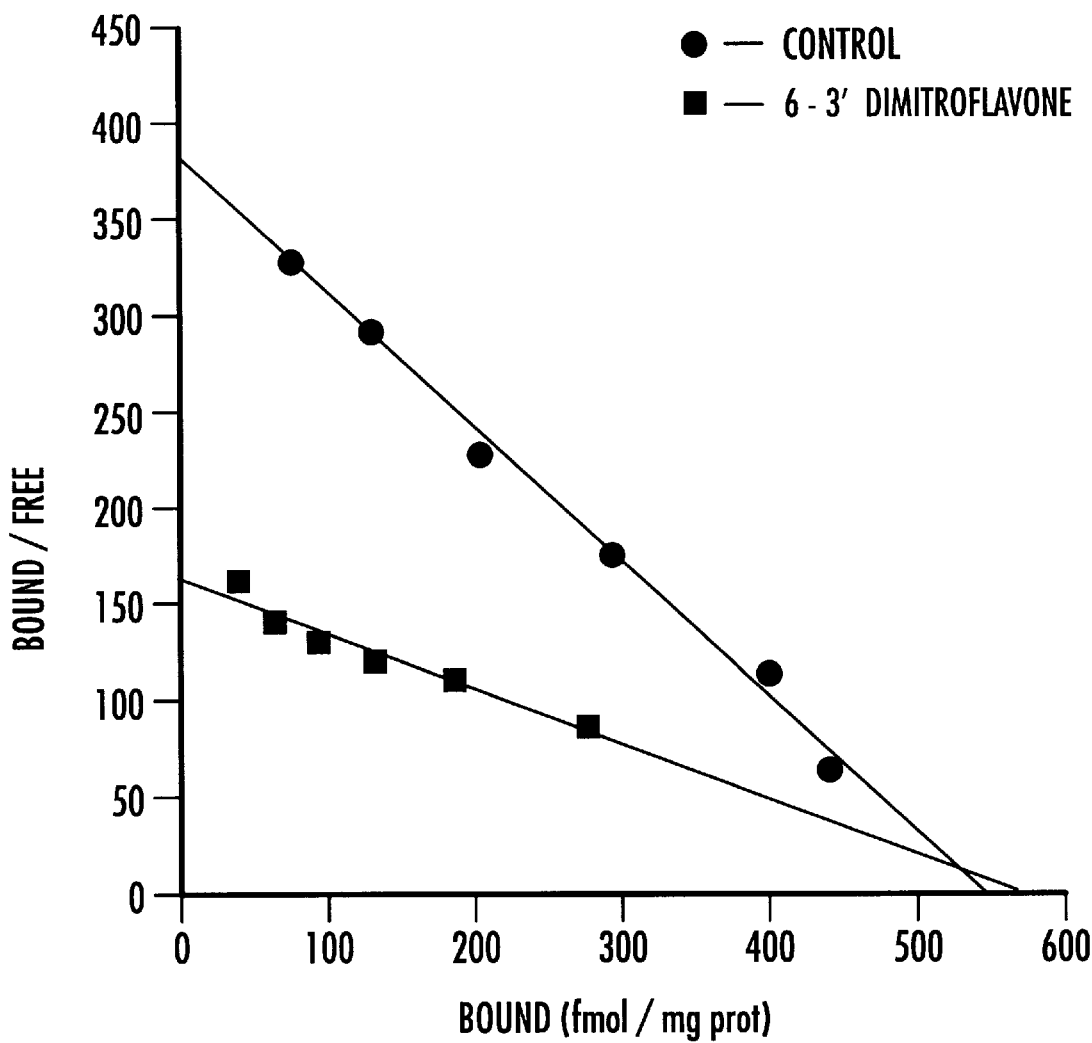

United States Patent [19]
Paladini et al.

[11] Patent Number: 6,080,780
[45] Date of Patent: Jun. 27, 2000

[54] USE OF NITROFLAVONOIDS FOR THE TREATMENT OF ANXIETY

[75] Inventors: Alejandro Constantino Paladini; Jorge Horacio Medina, both of Buenos Aires, Argentina

[73] Assignee: University of Strathclyde, United Kingdom

[21] Appl. No.: 09/051,758

[22] PCT Filed: Oct. 16, 1996

[86] PCT No.: PCT/GB96/02523

§ 371 Date: Jul. 8, 1998

§ 102(e) Date: Jul. 8, 1998

[87] PCT Pub. No.: WO97/14414

PCT Pub. Date: Apr. 24, 1997

[30] Foreign Application Priority Data

Oct. 17, 1995 [GB] United Kingdom .................. 9521184

[51] Int. Cl.[7] ...................... A61K 31/35; C07D 311/04; C07D 311/74
[52] U.S. Cl. .................. 514/456; 514/457; 549/399; 549/400; 549/401; 549/404; 549/406
[58] Field of Search .................. 549/399, 401, 549/400, 404, 406; 514/457, 456

[56] References Cited

FOREIGN PATENT DOCUMENTS

95/05169   2/1995   WIPO .

OTHER PUBLICATIONS

Shah et al, Chemical Abstract vol. 95 No. 97521, "Flavones, flavonols and flavanones derived from 2'—hydroxy-4'-n-propoxy-5'-nitrochalcones" (1980).

Flammang et al, Chemical Abstract vol. 89 No. 146720, "Effects of the mature and the position of substituents in a novel synthesis method of B-flavanols" (1978).

Philippe, Chemistry Abstract vol. 78 No. 136075, "Hypotensive and analgesic 7-hydroxychromauones and semicarbazone derivatives", (1973).

*Primary Examiner*—John Kight
*Assistant Examiner*—Raymond Covington
*Attorney, Agent, or Firm*—Alston & Bird LLP

[57] ABSTRACT

Methods of treating anxiety with flavonoid compounds according to Formula (I) and dimers thereof, compounds of Formula (I) and dimers thereof, use of compounds of Formula (I) and pharmaceutical formulations comprising flavonoids of Formula (I) and dimers thereof.

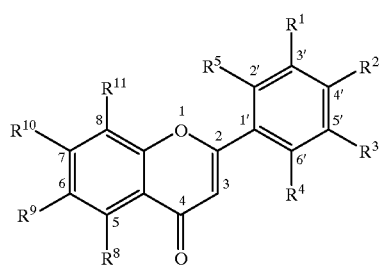

42 Claims, 10 Drawing Sheets

USE OF NITROFLAVONOIDS FOR THE TREATMENT OF ANXIETY

FIELD OF INVENTION

The present invention relates to flavonoids which have been found to have anxiolytic properties (i.e. anxiety reducing) without corresponding depression of the central nervous system which is commonly also found in known sedatives such as benzodiazepines. In particular, the present invention relates to flavonoids comprising nitro groups located on the phenyl ring and analogues thereof.

BACKGROUND

Co-pending patent application WO 95/05169 (Strathclyde University) relates to flavonoids and their use in methods of treating anxiety in patients. The flavonoids of WO 95/05169 are described as having anxiolytic properties without associated depression of the central nervous system (e.g. sedative and muscle relaxant effects) commonly found with benzodiazepines. The compounds of WO 95/05169 fall under a general formula:

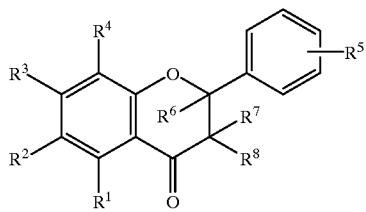

wherein $R^1$, $R^2$, $R^3$ and $R^4$, $R^5$ and $R^8$ are independently selected from H, OH, R, $NO_2$, halo, OR, $NH_2$, NHR, $NR_2$, COOR, COOH, CN, or a sugar group;

$R^6$ and $R^7$ are both H, or $R^6$ and $R^7$ together form a single bond;

R is $C_{1-6}$ alkyl or alkenyl; or dimers thereof.

Preferred compounds of WO 95/05169 are described in halo derivatives, in particular where $R^5$ is halo at the 2' position of the above general formula.

It has now been found that certain compounds falling within the generic formula of WO 95/05169 exhibit unexpectedly good anxiolytic activity without associated depression of the central nervous system (e.g. sedative and muscle relaxant effects) commonly found with benzodiazepines, when the flavone nucleus and/or phenyl ring comprises at least one $NO_2$ substituent. Thus, patients may be treated for anxiety without inducing sedative or myorelaxant side-effects.

It has also been found that compounds of the present invention display a substantially reduced or no anticonvulsant effect, and that memory is apparently not adversely affected, side-effects commonly found with benzodiazepines.

STATEMENT OF INVENTION

According to the present invention there is provided a method of treating anxiety in a patient which comprises administering to the patient an effective non-toxic amount of a flavonoid of general formula (I):

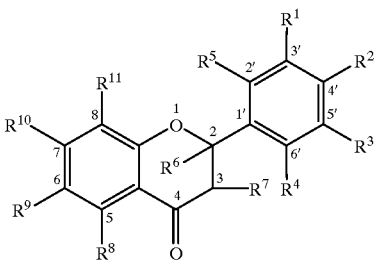

wherein $R^1$, $R^2$, $R^3$, $R^4$ and $R^5$ are independently selected from $NO_2$ and H;

$R^6$ and $R^7$ are independently selected from Br, Cl, F, and H or $R^6$ and $R^7$ together form a single bond;

$R^8$, $R^{10}$ and $R^{11}$ are independently selected from H, —OH, —R, —$NO_2$, Br, Cl, F, —OR, —$NH_2$, —NHR, —$NR_2$, —COOR, —COOH, —CN or a sugar group;

$R^9$ is selected from H, $NO_2$, Br, Cl, or F;

R is $C_1$–$C_6$ alkyl or alkenyl;

with the proviso that at least one of $R^1$, $R^2$, $R^3$, $R^4$ and $R^5$ is $NO_2$ and with the exception that when $R^9$ is H, $R^5$ is H.

or the administration of an effective non-toxic amount of a bi-flavonoid which is a dimer of a compound of general formula (I) and wherein $R^1$ to $R^{11}$ and R have the meanings given for general formula (I).

The sugar group may be any of the known sugars, including monosaccharides, disaccharides and polysaccharides; and may in particular be glycosyl, galactopyranosyl or mannopyranosyl.

Preferred compounds of Formula I include compounds wherein $R^1$, $R^2$ and $R^5$ are independently selected from $NO_2$ and H;

$R^8$, $R^{10}$ and $R^{11}$ are all hydrogen;

$R^9$ is selected from H, $NO_2$, Br, Cl and F; with the proviso that at least one of $R^1$, $R^1$ and $R^5$ is $NO_2$ with the exception that when $R^9$ is H, $R^5$ is H.

More preferred compounds of Formula (I) are those wherein $R^1$, $R^2$ and $R^5$ are independently selected from H and $NO_2$;

$R^6$ and $R^7$ together form a single bond;

$R^8$, $R^{10}$ and $R^{11}$ are all hydrogen;

$R^9$ is selected from H, $NO_2$, Br, Cl and F; with the proviso that at least one of $R^1$, $R^2$ and $R^5$ is $NO_2$ with the exception that when $R^9$ is H, $R^5$ is H.

Most preferred compounds of Formula (I) are those wherein $R^1$, $R^2$ and $R^5$ are independently selected from $NO_2$ and H;

$R^3$, $R^1$, $R^8$, $R^{11}$ are all H;

$R^6$ and $R^7$ together form a single bond;

$R^9$ is selected from Br, Cl, F and $NO_2$;

with the proviso that at least one of $R^1$, $R^2$ and $R^5$ is $NO_2$.

Examples of preferred compounds of formula (I) for use in treating anxiety in a patient include:

6,3'-dinitroflavone

3'nitroflavone

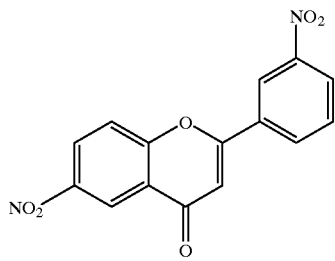
(II)

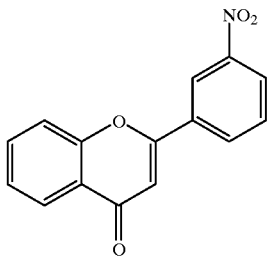
(VI)

4'nitroflavone

6, Bromo, 2'nitroflavone

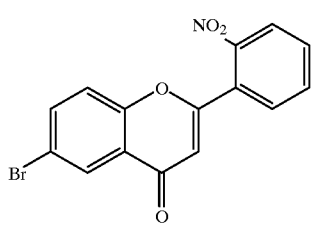
(III)

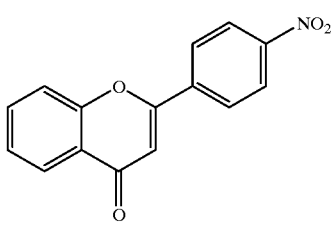
(VII)

6, chloro, 3'nitroflavone

6, Bromo, 3'nitroflavone

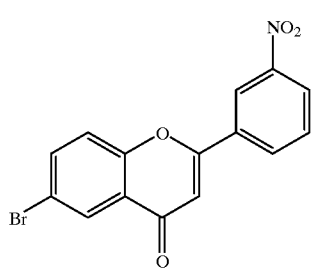
(IV)

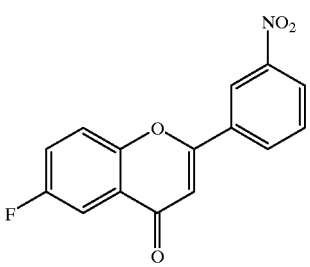
(VIII)

6, fluoro, 3'nitroflavone

6, Bromo, 4'nitroflavone

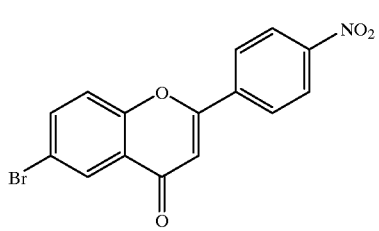
(V)

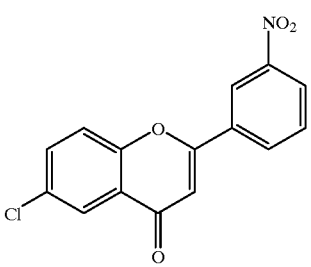
(IX)

Especially preferred are compounds (II) (IV), and (VIII) above.

Compounds wherein $R^6$ and $R^7$ together form a single bond are flavone derivatives, whereas compounds wherein $R^6$ and $R^7$ are both H are flavanone derivatives.

The bi-flavonoid is a dimer of two covalently bonded moieties which are each of general formula (I) as set forth above. Bonding between the two moieties generally occurs at the 3'-position of one moiety and 8-position of the other moiety. The preferred bi-flavonoid has general formula (X) wherein $R^1$ to $R^{11}$ and R have the same meanings as for general formula (I):

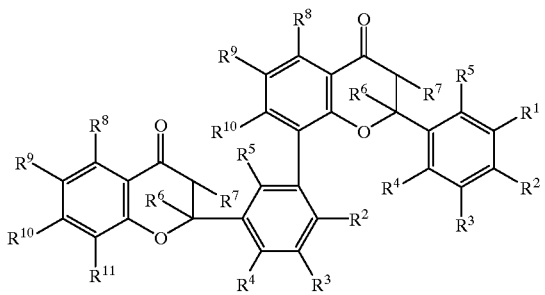

(X)

The compounds of general formula (X) wherein at least one of $R^1$ and $R^2$ in each of the dimer moieties of general formula (I) is $NO_2$; $R^9$ is selected from Cl, Br, F and $NO_2$; $R^6$ and $R^7$ are both H or $R^6$ and $R^7$ together form a single bond; and all other R functional groups are hydrogen are preferred.

The compounds of general formula (X) wherein the compounds are 3' or 4'nitro containing compounds; $R^4$ is selected from $NO_2$, Cl and Br; $R^6$ and $R^7$ are both H or $R^6$ and $R^7$ together form a single bond; and all other R functional groups are hydrogen are more preferred.

Pharmaceutical formulations include at least one compound of general formula (I) and/or (X) together with at least one pharmaceutically acceptable carrier or excipient. Naturally, the skilled addressee will appreciate that compounds of the invention employed in pharmaceutical formulations of the invention possess R groups $R^1$ to $R^{11}$ and R as defined herein. Each carrier must be "pharmaceutically acceptable" in the sense of being compatible with the other ingredients of the formulations and not injurious to the patient.

It should be understood that the flavonoid compounds of the present invention can be administered in the form of pharmaceutically acceptable salts or esters thereof. Salts are usually acid addition salts (e.g. with hydrohalogen acids) or acceptable metal salts (e.g. Na, Ca, Mg).

Formulations include those adapted for oral, rectal, nasal, vaginal and parenteral (including subcutaneous, intramuscular, intravenous and intradermal) administration. The formulations may conveniently be presented in unit dosage form and may be prepared by any methods well known in the art of pharmacy. Such methods include the step of bringing into association the active ingredient with the carrier which constitutes one or more accessory ingredients. In general, the formulations are prepared by uniformly ad intimately bringing into association the active ingredient with liquid carriers or finely divided solid carriers or both, and then if necessary shaping the product.

Formulations of the present invention adapted for oral administration may be presented as discrete units such as capsules, sachets or tablets each containing a predetermined amount of the active ingredient; as a powder or granules; as a solution or a suspension in an aqueous or on-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g. povidone, gelatin, hydroxypropylmethylcellulose), lubricant, inert diluent, preservative, disintegrant (e.g. sodium starch glycolate, cross-linked povidone, cross-linked sodium carboxymethylcellulose) active-surface or dispersing agent. Moulded tablets may be made by moulding in a suitable machine a mixture of the powdered compound moistened with an inert liquid diluent. The tablets may optionally be coated or scored and may be formulated so as to provide controlled release of the active ingredient therein using, for example, hydroxypropylmethylcellulose in varying proportions to provide the desired release profile.

Formulations for rectal administration may be presented as a suppository with a suitable base comprising for example cocoa butter or a salicylate.

Formulations for vaginal administration may be presented as pessaries, tampons, creams, gels, pastes, foams or spray formulations containing in addition to the active ingredient such carriers as are known in the art to be appropriate.

Formulations are parenteral administration include aqueous and non-aqueous isotonic sterile injection solutions which may contain anti-oxidants, buffers, bacteriostatis and solutes which render the formulation isotonic with the blood of the intended recipient; and aqueous and non-aqueous sterile suspensions which may include suspending agents and thickening agents. The formulations may be presented in unit-dose or multi-dose sealed containers, for example, ampoules and vials, and may be stored in a freeze dried (lyophilized) condition requiring only the addition of the sterile carrier, for example water for injections, immediately prior to use. Extemporaneous injection solutions and suspensions may be prepared from sterile powders, granules and tablets of the kind previously described.

The dose will depend on a number of factors known to the skilled physician including the severity of the conditions, the identity of the recipient; and also the efficacy and toxicity of the particular compound of general formula (I) which is being administered. Generally doses in the range 0.1–100 mg/kg body weight may be used, particularly 1–10 mg/kg. The frequency of administration will vary depending on the rate of metabolism or excretion of the administered compound, but may be repeated daily, optionally as two or more sub-doses. Unit doses of 20 to 500 mg, preferably 100 to 400 mg may be used.

As a further aspect of the present invention there is provided a compound of general Formula (I)

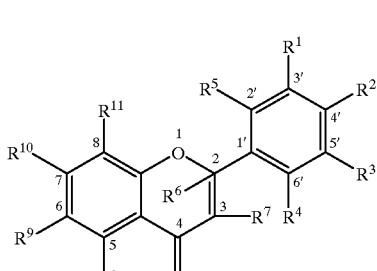

(I)

wherein
$R^1$, $R^2$, $R^3$, $R^4$ and $R^5$ are independently selected from $NO_2$ and H;
$R^6$ and $R^7$ are independently selected from Br, Cl, F, and H or $R^6$ and $R^7$ together form a single bond;

$R^8$, $R^{10}$ and $R^{11}$ are independently selected from H, —R, $NO_2$, Br, Cl, F, —OR, —$NH_2$, —NHR, —$NR_2$, —COOR, —COOH, —CN or a sugar group;

$R^9$ is selected from H, $NO_2$, Br, Cl, or F;

R is $C_1$–$C_6$ alkyl or alkenyl;

with the proviso that at least one of $R^1$, $R^2$, $R^3$, $R^4$ and $R^5$ is $NO_2$ and with the exception that when $R^9$ is H, $R^5$ is H.

or a bi-flavonoid which is a dimer of a compound of general Formula (I) and wherein $R^1$ to $R^{11}$ and R have the meanings given for general Formula (I).

Preferred compounds of Formula (I) include compounds wherein $R^1$, $R^2$ and $R^5$ are independently selected from $NO_2$ and H;

$R^8$, $R^{10}$ and $R^{11}$ are all hydrogen;

$R^9$ is selected from H, $NO_2$, Br, Cl and F; with the proviso that at least one of $R^1$, $R^2$ and $R^5$ is $NO_2$ and with the exception that when $R^9$ is H, $R^5$ is H.

More preferred compounds of Formula (I) are those wherein $R^1$, $R^2$ and $R^5$ are independently selected from H and $NO_2$;

$R^6$ and $R^7$ together form a single bond;

$R^9$ is selected from H, $NO_2$, Br, Cl and F; with the proviso that at least one of $R^1$, $R^2$ and $R^5$ is $NO_2$ and with the exception that when $R^9$ is H, $R^5$ is H.

Most preferred compounds of Formula (I) are those wherein $R^1$, $R^2$ and $R^5$ are independently selected from $NO_2$ and H;

$R^3$, $R^4$, $R^8$, $R^{11}$ are all H;

$R^6$ and $R^7$ together form a single bond;

$R^9$ is selected from Br, Cl, F and $NO_2$;

with the proviso that at least one of $R^1$, $R^2$ and $R^5$ is $NO_2$.

Preferred compounds of the invention include 6, 3'-dinitroflavone and 6 halogen, 3'-nitro or 6 halogen, 4'-nitroflavones and derivatives thereof. Examples of preferred compounds of the invention include:

6,3'-dinitroflavone

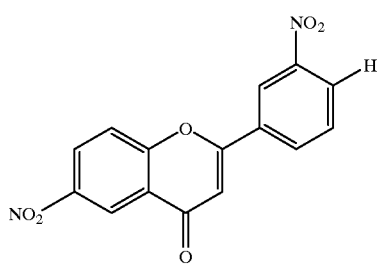

(II)

6, Bromo, 2'-nitroflavone

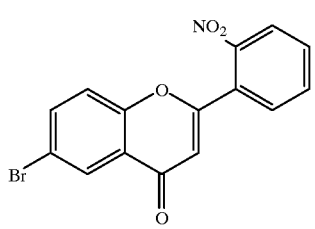

(III)

6, Bromo, 3'nitroflavone

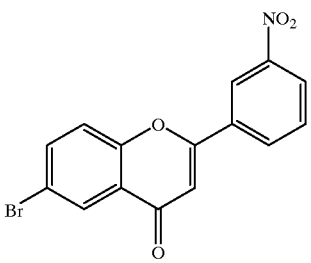

(IV)

6, Bromo, 4'nitroflavone

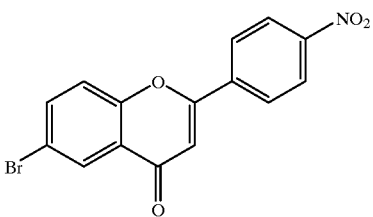

(V)

3'nitroflavone

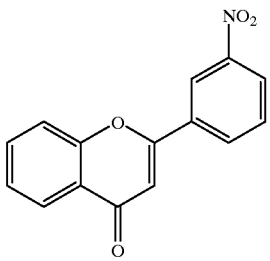

(VI)

4'nitroflavone

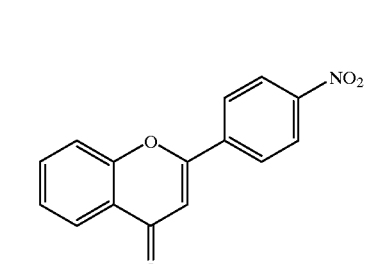

(VII)

6, chloro, 3'nitroflavone

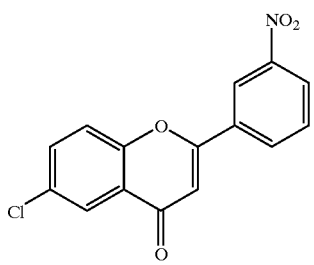

(VIII)

6, fluoro, 3'nitroflavone

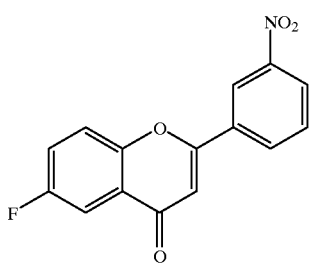

(IX)

Most preferred compounds of the invention are II, IV and VIII.

In a further aspect of the invention there is provided use of compounds of Formula (I) in the preparation of a medicament for the treatment of anxiety in a patient. In a preferment there is provided use of a compound according to any one or more of formulae (II), (III) to (IX) and (X) in the preparation of a medicament for the treatment of anxiety in a patient. More preferably there is provided use of a compound or a cocktail of compounds selected from compounds (II), (IV) and (VIII) in the preparation of a medicament for the treatment of anxiety in a patient.

The invention will now be illustrated by reference to the following figures.

FIG. 1:

Scatchard plot of representative curves of $^3$H-Flunitrazepam ($^3$H-FNZ) binding to bovine synaptosomal membranes in the absence (●) or in the presence of compound II (■, 20 nM).

FIG. 2:

Performance of mice during a 5 minute test on the elevated plus-maze test, 15 minutes after i.p. injection with vehicle (VEH) or compound (II) (0.3–100.0 μg/Kg). Results are expressed as mean ±SEM of the number of total arms entries (hatched bars), percentage of open arms entries (open arms) and percentage of time spent in the open arms (closed bars). *: p<0.05, **: p<0.01, Dunnet's multiple comparison test. The number of experimental mice per group used ranged between 9–16.

FIG. 3:

Competition by 6, 3'-dinitroflavone of [$^3$H]-FNZ binding to extensively washed crude synaptosomal membranes from various rat brain regions. Membranes from cerebellum (■), cerebral cortex (O) and spinal cord (▼) were prepared as described in Material and Methods. Data are from a representative experiment replicated 6–8 times.

FIG. 4:

Competition experiments by inhibiting 0.65 nM [$^3$H]-FNZ binding sagittal sections of the rat brain with various concentrations of 6,3'-dinitroflavone. Preparation of brain sections for autoradiographic analysis was described in Material and Methods. Representative displacement curves from cerebellum (■); parietal cortex (O) and dentate gyrus (▼) are shown.

FIG. 5:

Ambulatory locomotor activity counts during a 5-min test session in a Opto-varimex® apparatus 15 min after an i.p. injection of vehicle (VEH) or 6,3'-dinitroflavone (DNF, 0.001–10 mg/kg as detailed). Data are expressed as mean ±S.E.M. Number of animals in the experimental groups ranged between 10 and 16. *p<0.05, **p<0.01, significantly different from controls (Dunnett's multiple comparison tests after ANOVA).

FIG. 6:

Mean ±S.E.M. of total entries (open bars), percentage of open arm entries (hatched bars) and percentage of time spent in open arms (closed bars) of mice given a 5 min session in the elevated plus maze 20 min after i.p. injection of vehicle (VEH), 6,3'-dinitroflavone (DNF, 30 μg/kg) or DNF (30 μg/kg)÷Ro 15 1788 (1 mg/kg). *p<0.01, significantly different from controls (Dunnett't-test after ANOVA). Number of animals per group is shown in parentheses.

FIG. 7:

Mean ±S.E.M. number of head dips (closed bars) and time (in seconds) spent head-dipping (hatched bars) of mice given a 5 min session in the hole board test 20 min after an i.p. injection of vehicle (VEH) or 6,3'-dinitroflavone (DNF, 0.3–10 mg/kg). *p<0.01, significantly different from controls (Dunnett's t-test after ANOVA). Number of animals per group is shown in parentheses.

FIG. 8:

Performance of mice in the horizontal wire test after an i.p. injection of vehicle (VEH) or 6,3'-dinitroflavone (DNF, 0.3–10 mg/kg). The session test took place after two trials, executed after a 5 min interval (see Materials and Methods). Number of animals per group is shown in parentheses.

FIG. 9:

Performance of mice in the horizontal wire test 20 min after an i.p. injection of diazepam (DZ, 1 mg/kg) or 6,3'-dinitroflavone (DNF, 1 mg/kg)÷diazepam (DZ, 1 mg/kg). The session test took place after two trials, executed after a 5 min interval (see Material and Methods). *p<0.0001, Chi square frequency test. Number of animals per group is shown in parentheses.

FIG. 10:

Effect of pre-training and post-training i.p. administration of vehicle (open bars) or 100 μg/kg or 6,3'-dinitroflavone (hatched bars) in memory of an inhibitory avoidance test. The ordinate represents the step-down latency (in seconds) of the test session. Data are expressed as medians (interquartile range). Number of animals per group is shown in parentheses.

FIG. 11:

Shows that binding of 0.5 nM $^3$H-FNZ, to extensively washed crude synaptosomal membranes from rat cerebellum (●), cerebral cortex (O) and spinal cord (▼), was displaced by 9–14 different concentrations of compound (IV). Data are from a representative experiment replicated 3–6 times. The competition curves were analysed using the Graph-pad software (see results in Table 5).

FIG. 12:

Mean ±S.E.M. of total arms entries (open bars), percentage of open arms entries (closed bars) and percentage of time spent in the open arms (hatched bars) of mice given a 5 min session in the elevated plus-maze, 20 min after i.p. injection with vehicle (VEH) or 100 μg/kg of compound (IV). *p<0.01, Student t test. Number of animals per group= 17.

There now follow examples which illustrate the invention. It is to be understood that the examples are not intended to limit the scope of the invention in any way.

EXAMPLES SECTION 1

Example 1:

Preparation of 6,3'-Dinitroflavone (II) and 6,4'-Dinitroflavone (IIa)

6,3'-Dinitroflavone (II) and 6,4'-dinitroflavone (IIa) were prepared as follows (Scheme A):

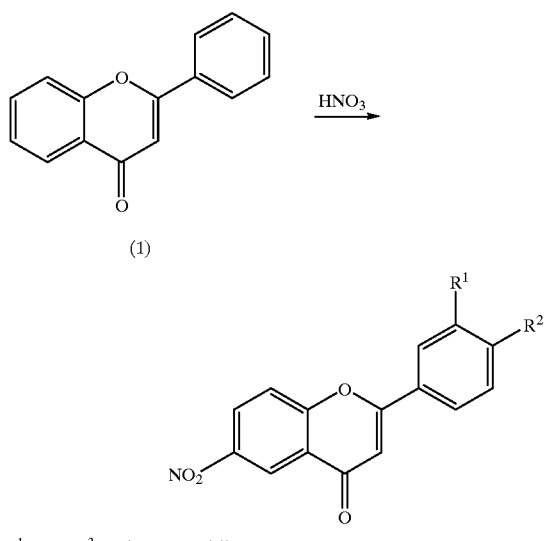

$R^1 = NO_2$; $R^2 = H$ (Compound (II))
$R^1 = H$; $R^2 = NO_2$ (Compound (IIa))

Anhydrous nitric acid (d=1.4, 750 µL) was added dropwise to flavone (1) (Extrasynthese, France) (60 mg; 0.27 mmol).

The vial containing (1) was kept in an ice bath during the addition. The resulting solution was allowed to stand for 30 minutes at room temperature. While stirring with a thin glass rod, water (10 mL) was added, and the vial placed in an ice bath to cool. The precipitated product was collected by vacuum filtration, washed with water and dried. Its toluene solution was chromatographed in a silica gel column which was eluted in steps with increasing concentrations of acetone in toluene. Two major components could be isolated which were further purified by recrystallisation from acetone-water rendering compounds (II) and (IIa). Compound (II): yield 45%; yellow light crystals (from acetone-water);

mp 246–248° C.; $^1$H NMR (300 MHz, DMSO-$d_6$): δ 8.90 (t, J=2 Hz, 1H), 8.72 (d, J=2.6 Hz, 1H), 8.64 (dd, J=9.3 and 2.6 Hz, 1H), 8.59 (m, 1H), 8.46 (m,1H), 8.16 (d, J=9.3 Hz, 1H), 7.89 (t, J=8.4 Hz, 1H), 7.43 (s, 1H). EIMS m/z 312 [M]$^+$, 284, 266, 238, 220, 165.

Compounds (IIa) yield 45%, yellow crystals (from acetone-water);

mp 260–261° C.; $^1$H NMR (300 MHz, DMSO-$d_6$); δ 8.72 (s, 1H), 8.65 (d, J=9.1 Hz, 1H), 8.40 (m, 4H), 8.10 (d, J=9.2 Hz 1H), 7.42 (s, 1H). EIMS m/z 312 [M]$^+$, 284, 266, 254.

RESULTS

Non-specific nitration of the flavone nucleus yielded the two nitrated flavone (II) and (IIa). Compounds (II) and (IIa) inhibited $^3$H-Flunitrazepam ($^3$H-FNZ) binding extensively washed bovine cerebral cortical membranes with a Ki of 12.0±1.7 nM (n=7) and 17±5 µM (n=3), respectively. Briefly, $^3$H-FNZ binding was carried out as described by Levy de Stein, M., Medina, J. H., De Robertis E., Mol. Brain Res. 1985, 5, 9–15. In brief, for each assay, triplicate samples of the membranes, containing 0.2 to 0.4 mg protein were suspended in a final volume of 1 mL of 0.25 mM Tris-HCl buffer, pH 7.3. The incubation was carried out at 4° C. for 60 minutes with 0.6 nM $^3$-FNZ. To study the binding saturation, a range of 0.3 to 10 nM $^3$H-FNZ was used. Non-specific binding was determined in parallel incubations in the presence of 3 µM FNZ, and represented 5–15% of total. The assays were terminated by filtration under vacuum though Whatman GF/A glass-fiber filters, and three washes with 3 mL each of incubation medium. Filters were dried and counted after the addition of 5 mL of 2,5-diphenyloxazole/xylene as scintillation fluid. Bovine cerebral cortical membranes were treated substantially following the method of Medina, J. H., De Robertis, E. J., J. Neurochem. 1985, 44, 1340–1345. Scatchard analysis of saturation curves for compound (II) revealed a competitive interaction showing a decline in the apparent affinity without changes in the maximal number of sites (Bmax) (FIG. 1). Compound (II) showed a very high affinity for the benzodiazepine (BDZ-R) receptor.

Example 2

Pharmacological Activity: Performance of Mice on the Elevated Pluz-Maze.

As compound (II) showed a very high affinity for the BDZ-R it was further examined for pharmacological activity. Performance of mice on the elevated plus-maze test was used to measure anxiolytic actions in rodents, following i.p. administration of vehicle or compound (II).

The animals used in the pharmacological test were male Swiss mice from breeding stock, weighing 28–35 g. They were placed n groups of ten with free access to water and food, and maintained on 12 h/12 h day/night cycle. In all the tests the mice were i.p. injected with VEH or a solution of the drug, 15 minutes before the assay.

Figure 2:
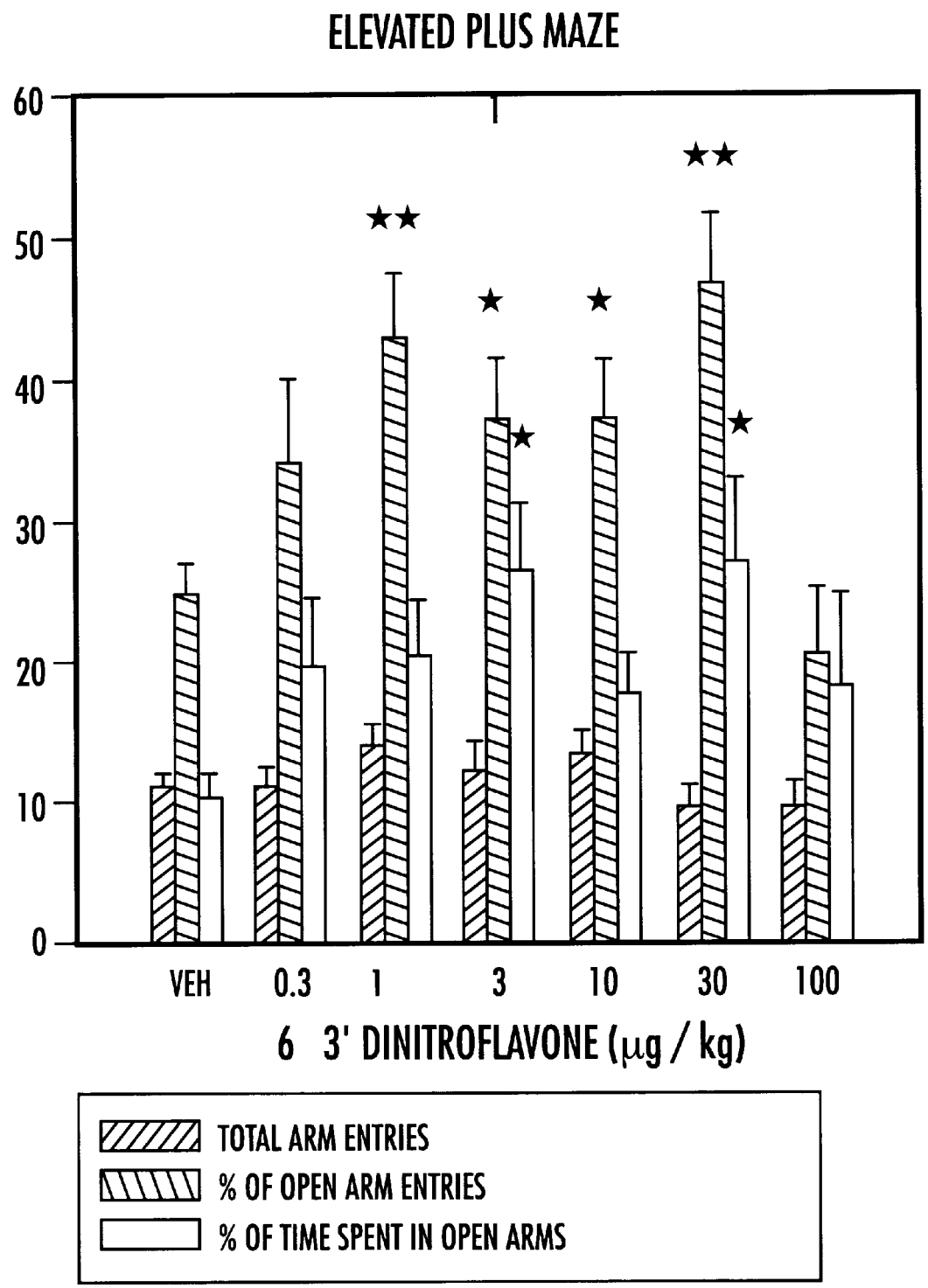

The elevated plus-maze set-up consisted of a maze of two open arms, 25×5 cm, crossed by two closed arms of the same dimensions, with free access to all arms from the crossing point. The closed arms had walls 35 cm high all around. The maze was suspended 50 cm from the room floor. Mice were placed on the central part of the cross facing an open arm. The number of entries and the time spent going into open and closed arms were counted during 5 minutes. A selective increase in the parameters corresponding to open arms reveals an anxiolytic effect. The total exploratory activity (number of entries in both arms) was also determined. Results are shown in FIG. 2.

Compound (II) at doses ranging from 0 to 30 µg/kg increased the percentage of entries in the open arms, without affecting the total arm entries. It is important to stress that for diazepam a minimum dose of 30 µg/kg is necessary in order to produce similar anxiolytic effects (data not shown). At a dose of 3 and 30 µg/kg, (II) also enhanced the percentage of the time spent in the open arms (FIG. 2).

In conclusion, it appears that (II) is a very potent anxiolytic drug that interacts competitively and with high affinity with the BDZ-R.

Comparative anxiolytic concentration ranges of halo derivatives of WO 95/05169 and diazepam to compound (II) are shown below:

TABLE 1

| Compound | Anxiolytic Concentration (μg/kg) |
| --- | --- |
| Compound (II) | 0.3–30 |
| 6 Bromoflavone | 500–3000 |
| 6,8 dibromochrysin | 1000–3000 |
| 2'chlorochrysin | 1000 |
| 2'fluorochrysin | 1000 |
| Diazepam | 30–1000 |

EXAMPLES SECTION 2

Materials and Methods

Animals

Adult male Wistar rats weighing 250 g were used for biochemical experiments. Adult male Swiss male weighing 25–30 g were used for pharmacological assays except for inhibitory avoidance and tail flick tests were done in rats. Animals were housed in a controlled environment, with free access to food and water and maintained on a 12 h/12 h day/night cycle.

Radioreceptor Binding Assays

Displacement curves were performed using [$^3$]-FNZ or [$^3$H]-zolpidem ([$^3$H]-ZOLP) as radioligands in washed crude synaptosomal membranes from rat cerebral cortex, cerebellum, hippocampus, striatum or spinal cord. Membrane preparations were carried out according to Medina et al. (1990). Briefly, brains were rapidly dissected out on ice and the different structures were homogenized in 10 volumes of 0.32 M sucrose and centrifuged at 900×g for 10 min. The resulting supernatant was centrifuged at 100,000×g for 30 min and the pellet washed twice in 25 mM Tris HCl buffer pH 7.4 at 100,000×g for 30 min, and stored at −20° C. until used.

For [$^3$H]-FNZ (84 Ci/mmol, NEN) displacement curves, different concentrations of DNF (0.3 nM to 1 μM) were added to 0.3 mg membrane protein suspended in 1 ml of 25 mM Tris HCl buffer in presence of 0.6 nM of the radioligand. Protein determination was carried out by using the method of Lowry et al. (1951). Nonspecific binding (<5%) was determined in parallel incubations with 10 μM FNZ (Hoffmann-La Roche). The incubation was carried out at 4° C. for 2 h. The assays were determined by filtration under vacuum through Whatman GF/A glass fiber filters, and two washes with 3 ml each of incubation medium. Filters were dried and counted after the addition of 5 ml 2,5-diphenyl-oxazole (PPO)-xylene as scintillation fluid.

For [$^3$H]-ZOLP (50.8 Ci/mmol, NEN) binding assays we used the technique of Arbilla et al. (1986), slightly modified as follows: displacement curves were done with 1 nM of the radioligand and 10 μM zolpidem to determine the nonspecific binding (<15%). The incubation of the samples (0.4 mg protein in 1 ml of 50 mM Tris HCl buffer, pH 7.4, 120 mM NaCl, 5 mM KCl) was carried out at 4' C. during 30 min. The reaction was stopped with 3 ml of the same buffer and 3 washes. The other steps were similar to the original technique.

Additional binding studies were performed as described elsewhere: [$^3$]-prazosin binding for $\alpha_1$ adrenergic receptors (Medina et al., 1984), [$^3$H]-dihidroalprenolol binding for $\beta$ adrenergic receptors (Medina et al. 1984), [$^3$H]-quinuclidinyl benzylate binding for muscarinic cholinergic receptors (Jerusalinksy et al., 1983), [$^3$H]-muscimol binding for GABA$_\lambda$ receptors (Medina et al., 1983) and [$^3$H]-8-Hydroxydipropylaminotetralin ([$^3$H]—OH—DPAT) binding for serotonin (5-HT$_{I\lambda}$) receptors (Nénonéné et al., 1984).

Autoradiographic Experiments

Wistar rats were decapitated and brains rapidly removed. Sagittal sections (15 μm in thickness) were prepared at −20° C. using a microtome-cryostat. The tissue slices were kept frozen at −70° C. until used. For DNF displacement curves to [$^3$H]—FNZ binding (0.65 nM), tissue sections were incubated for 60 min at 4° C. in 25 mM Tris HCl buffer, pH 7.4, in presence of different concentrations of DNF (1–600 nM). For non-specific binding we used 10 μM FNZ. The incubation was terminated by rinsing the sections for two min in cold buffer. Sections were briefly dipped in cold distilled water and dried rapidly under a stream of cold air (Niddam et al., 1987).

Autoradiograms were generated by apposing the slide-mounted tissue section to tritium-sensitive film (Hyperfilm Amersham) in a light-proof X-ray cassette at 4° C. for two weeks.

The optical densities from different brain regions were converted first to radioactive units and then to fmol/mm$^2$ using the [$^3$H] standards on the film with the aid of a computerized image densitometric analysis system (MCID 4.02). The values were normalized and the K$_i$ values were determined using a computerized program (Graph-Pad Prism) Bernabeu et al., 1995; Cammarota et al., 1995).

Pharmacological Procedures

Locomotor Activity Test

An Opto-varimex® apparatus was used according to Viola et al. (1994). The apparatus discriminates between total and ambulatory activities. An increase in the number of transitions through the beams reflects augmented locomotor activity. In this and all following tests in mice, animals were i.p. injected with the vehicle, or with DNF 20 min before the beginning of the tests. In each session, control mice were tested in parallel with those animals receiving drug treatment.

Elevated Plus Maze Test

The test was performed in the same session immediately after the locomotor activity measurement (Viola et al., 1994; Wolfman et al., 1994). This test is widely validated for rodents (Pellow et al., 1985, Pellow and File, 1986; Lister, 1987) and possesses several advantages over other tests for measuring anxiety (Dawson and Tricklebank, 1995). A selective increase in the number of entries in the open arms and the time spent in the open arms reveals an anxiolytic effect of the drug (Pellow et al., 1985; Pellow and File, 1986). A series of experiments with the injection of the selective central benzodiazepine receptor antagonist Ro 15-1788 (File and Pellow, 1986) was also carried out.

Holeboard Test

The test was performed according to Viola et al. (1994) and Wolfman et al. (1994). The number of head dips and the time spent head dipping were counted during 5 min. A decrease in these parameters reveals a sedative behaviour (File and Pellow, 1985).

Horizontal Wire Test

This test was carried out as previously described (Viola et al., 1994; Wolfman et al., 1994; Viola et al., 1995). The test took place after two trials, performed at 5 min intervals. A myorelaxant drug will impair mice to grasp the wire (Bonetti et al., 1982). The effect of DNF )1 mg/kg) on DZ-induced myorelaxation was also determined.

Sodium Thiopental—Induced Sleeping Time

Sodium thiopental (Abbott) (22 mg/kg) was i.p. injected 15 min after vehicle or DNF. The disappearance and reappearance of the righting reflex were considered indications of latency and duration of sleep, respectively (Anca et al., 1993).

Seizure Testing

The effects of DNF on pentylenetetrazole (PTZ)—induced convulsions were evaluated according to Medina et al., (1990) with slight modifications. PTZ (200 mg/kg) was administered i.p. to mice 15 min after injection of drug or vehicle. The number of mice presenting clonic convulsions was determined.

Inhibitory Avoidance Test

This test was performed according to Izquierdo et al., (1990). The training apparatus was a 50×25×25 cm acrylic box with a frontal glass panel and a floor made of parallel 1 mm caliber bronze bars spaced 0.8 mm apart. A 5 cm high, 7 cm wide formica platform was placed on the loft extreme of the box. Rats were placed on the platform and their latency to step-down placing their four paws on the grid was measured. On stepping-down they received a 0.35 mA, 2 s scrambled footshock and were withdrawn from the box (training session). The test session was carried out 20 h later and was similar to the training session in all respects except that the footshock was omitted. Test step-down latency (to a ceiling of 180 s) was taken as a measure of retention of inhibitory avoidance (Izquierdo et al., 1990).

Tail-Flick Test

This test was performed according to Siegfried et al. (1987). Analgesia was assessed with a tail-flick apparatus. Rats were wrapped in a towel and placed on the apparatus; the light source positioned below the tail was focused on a point 2.3 cm rostral to the tip of the tail. Deflection of the tail activated a photocell and automatically terminated the trial. Light intensity was adjusted so as to obtain a baseline tail-flick latency (TFL) of 3–6 s. A cut-off time of 10 s was used to prevent tissue damage. Briefly, the general procedure was as follows: a baseline TFL value was obtained for each animal. Following this, the rats were placed alone in a waiting cage. TFL value was measured 1 h after an i.p. injection of vehicle or DNF.

Drugs 6,3'-Dinitroflavone (DNF) and DZ (Hoffman-La Roche) were dissolved in dimethylsulfoxide 20%, ethanol 20%, in distilled water, Ro 15-1788 (Hoffman-La Roche) was dissolved in propyleneglycol 10% and dimethylsulfoxide 15% in distilled water. The volume of injection was 0.1 ml/10 g in mice and 0.1 ml/100 g in rats.

Statistical Analyses

The competition curves were analysed using the Graph-Pad Prism software. Analysis of variance (ANOVA) was used when several treatments in mice were compared. Post-hoc comparisons between individual treatment and controls were made using Dunnett's multiple comparisons test. Chi square frequency test was used when required. Non-parametric Mann-Whitney U test was used for inhibitory avoidance and TFL tests in rats.

RESULTS

Biochemical Studies

Figure 3:
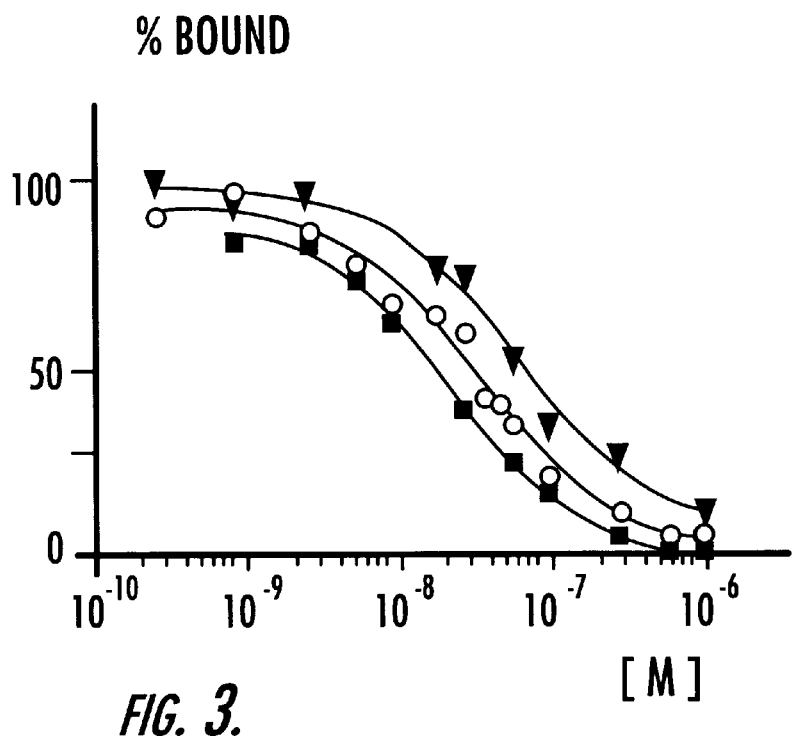

DNF had different potencies in displacing [$^3$H]—FNZ binding in various CNS regions (Table 2). It was more potent in the cerebellum, with a $K_i$ value of 17 nM; least potent in the striatum and spinal cord, with $K_i$ values of about 44–48 nM; and intermediate in potency in the cerebral cortex and hippocampus. FIG. 3 shows representative displacement curves of [$^3$H]—FNZ binding to cerebellar, cerebral cortical and spinal cord membranes by DNF (9–14 different concentrations). In contrast, the non-selective central benzodiazepine receptor agonist, DZ, displaced with similar $K_i$ the [$^3$H]—FNZ binding to all the brain regions studied (~7 nM).

Using [$^3$H]—ZOLP as the radioligand, a well known central benzodiazepine receptor agonist that recognizes preferentially the type I (Arbilla et al., 1986), DNF showed similar $K_i$ values in synaptosomal membranes from cerebral cortex, striatum and cerebellum (17.2±3.7 nM, n=5;21±nM, n=2 and 17±1.5 nM, n=3, respectively).

DNF (20 μM) did not displace the binding of [$^3$H]-quinuclidinyl benzilate, [$^3$H]-muscimol, [$^3$H]-prazosin, [$^3$H]-dihidroalprenolol and [$^3$H]-8-HO—DPAT to cholinergic muscarinic, $GABA_A$ $\alpha_1$ and $\beta$ adrenergic and 5-HT$_{1A}$ receptors, respectively (data not shown).

Similar region variations in the potency of DNF in displacing [$^3$H]—FNZ binding were observed in autoradiographic experiments (FIG. 2). The maximal inhibitory effect was observed in the cerebellum ($K_i$ 17.2±2.3 nM, n=3) followed by parietal cortex ($K_i$ 30.1±2.6 nM, n=3), striatum ($K_i$ 53.7±7.3 nM, n=3) and dentate gyrus ($K_i$ 82.2±7.6 nM, n=3).

Therefore, DNF is 5 times more potent to displace [$^3$H]—FNZ binding from the cerebellum than from the dentate gyrus.

TABLE 2

Inhibition constants of 6,3'-dinitroflavone displacing [$^3$H-FNZ binding to crude synaptosomal membranes from different regions of the rat CNS.

| Brain regions | n[a] | [$^3$H]-FNZ binding $K_i$ ± S.E.M., nM |
|---|---|---|
| Cerebellum | 6 | 17.2 ± 1.9 |
| Cerebral Cortex | 8 | 25.9 ± 3.1 |
| Hippocampus | 4 | 36.1 ± 5.0 |
| Striatum | 7 | 44.1 ± 4.9 |
| Spinal Cord | 4 | 48.1 ± 5.5 |

$K_i$ values were obtained by Graph-Pad Prism software from displacement curves of [$^3$H]-FNZ binding using 9–15 concentrations of 6,3'-dinitroflavone.
[a]number of independent experiments.

Pharmacological Experiments

Effect of DNF on Ambulatory Locomotor Activity

Figure 5:
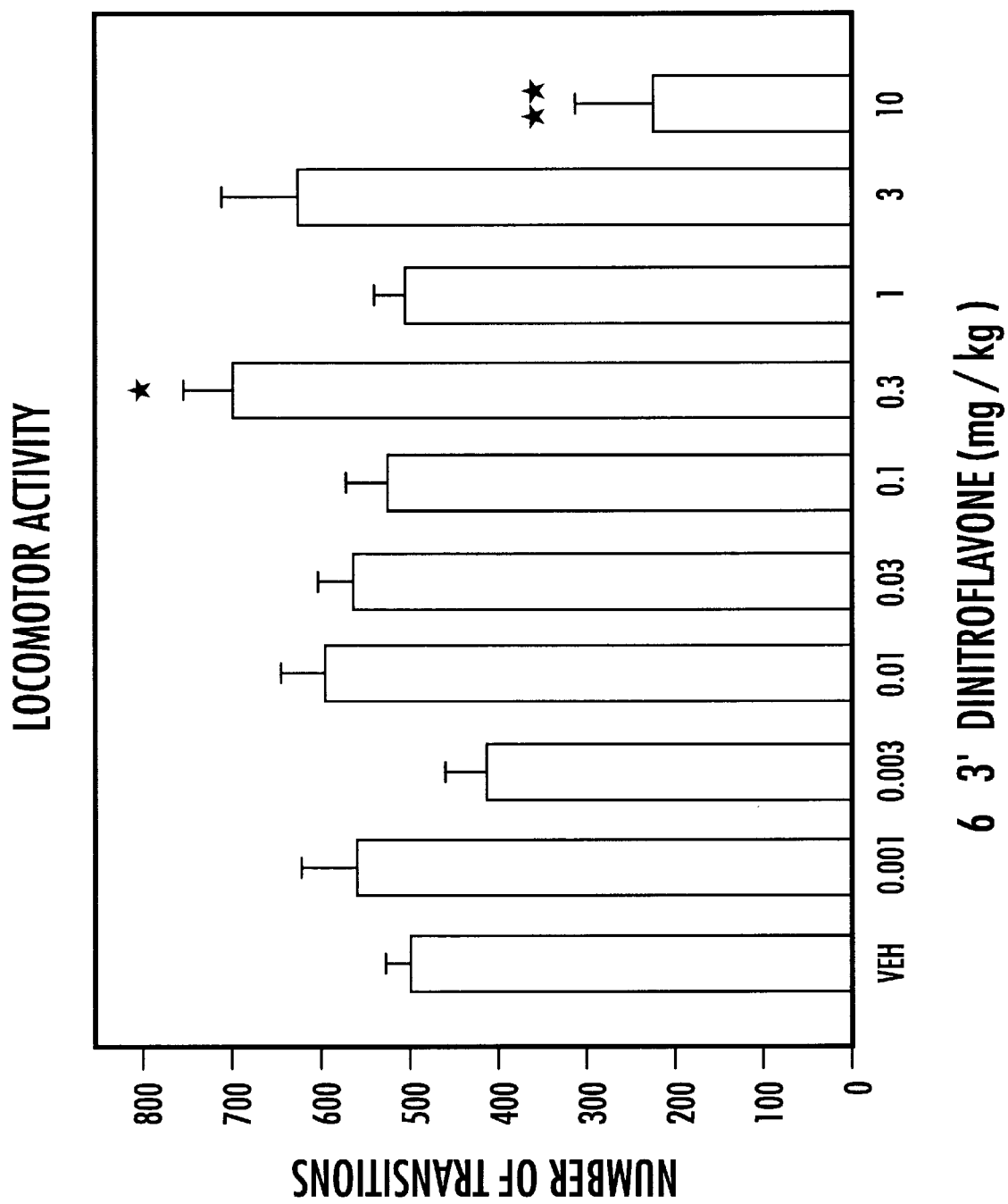

FIG. 5 shows that the i.p. administration of DNF (up to 3 mg/kg) had no effect on spontaneous ambulatory locomotion; at 10 mg/kg (the highest dose tested), there was a 55% reduction in the locomotion ($F_{(9.152)}$=4.52, p<0.01. A slight increase in this parameter was observed at 0.3 mg/kg (p<0.05.

Effect of DNF in the Elevated Plus Maze Test

Figure 6:
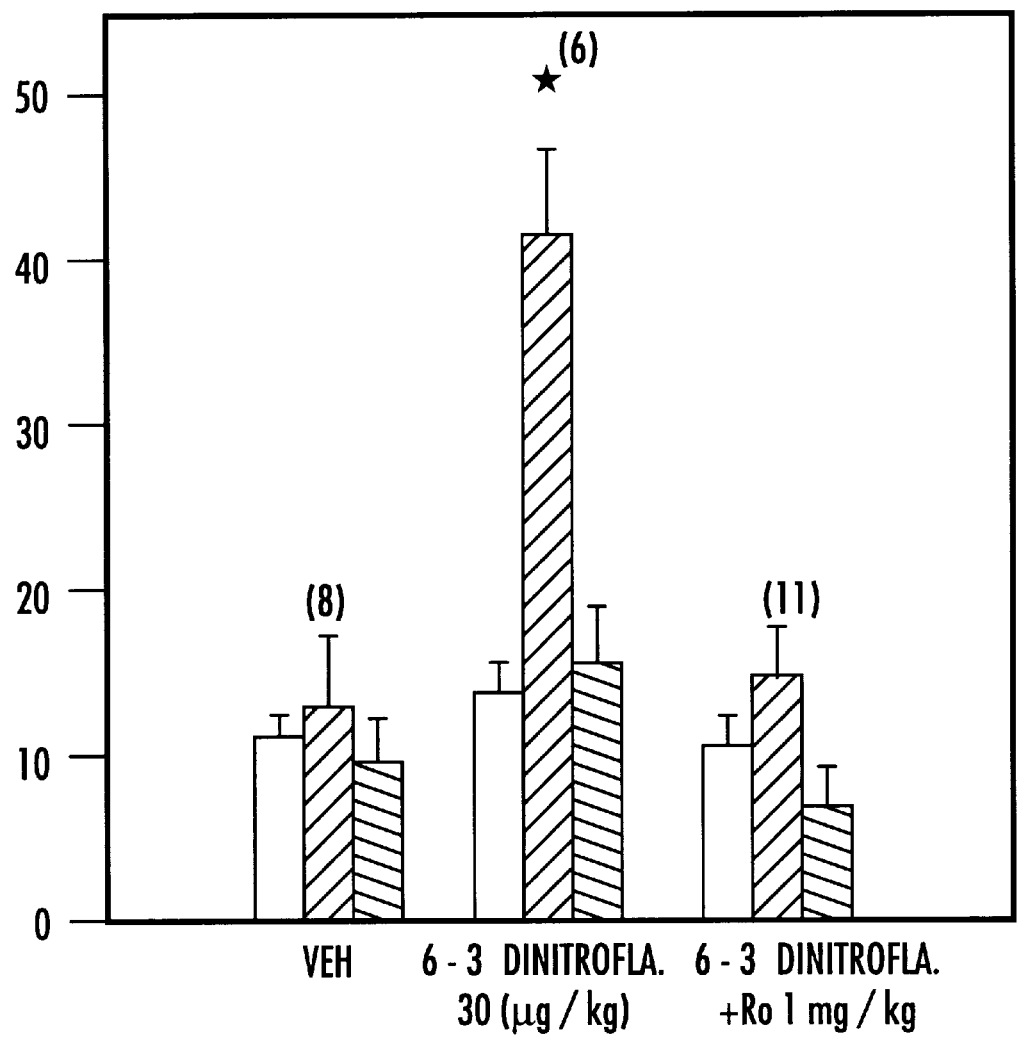
Figure 6:
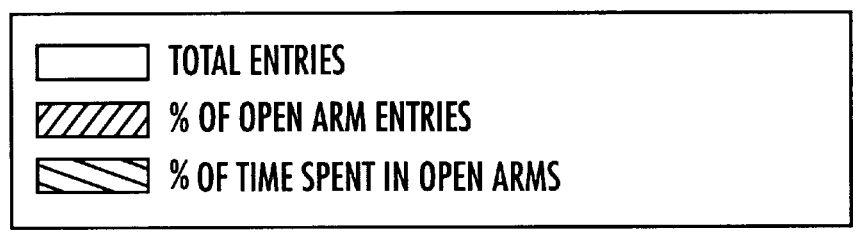

Previous experiments from our laboratory demonstrated that i.p. injection of low doses (1–30 μg/kg) of DNF in mice had anxiolytic effect as measured in this test. Confirming these results, i.p. administration of an anxiolytic dose of DNF (30 μg/kg) increased the percentage of entries in the open arms ($F_{(2.22)}$=13.37, p<0.01; Dunnett test after ANOVA) (FIG. 6). No differences were observed in the total arm entries ($F_{(2.22)}$=0.83, p<0.05). This anxiolytic effect was blocked by the injection of Ro 15-1788, a specific central benzodiazepine receptor antagonist (FIG. 6). Experiments run in parallel using DZ, revealed that this well known anxiolytic drug produced an increase in the percentage of open arm entries only at doses 10–100 times higher (vehicle=22.9±2.0%; DZ 0.3 mg/kg=35.0±4.5%, p<0.05; FIG. 6).

Effect of DNF in the Holeboard Test

Figure 7:
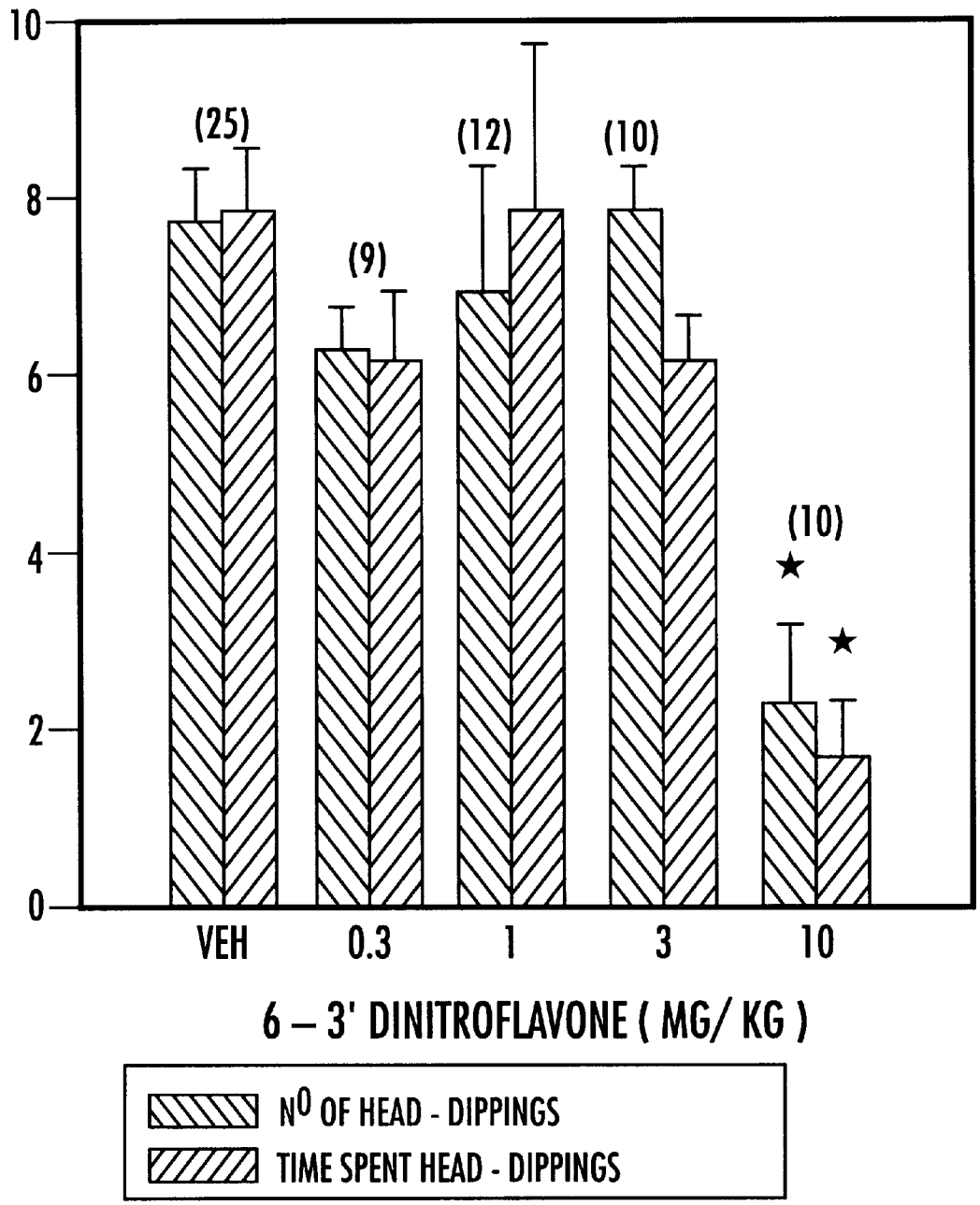

Performance of mice injected with vehicle or DNF in the holeboard test is shown in FIG. 7. As can be seen, doses up to 3 mg/kg did not change the number of head dips and the time spent head-dipping. Only at the high dose of 10 mg/kg (300 times higher than the anxiolytic dose used in this study), DNF decreased both parameters (F(head dips)$_{(2.01)}$= 6.04, F(time)$_{(2.01)}$=4.63, p<0.01; Dunnett comparison test after ANOVA). DZ provoked similar effects when injected at 1 mg/kg (head dips, vehicle=8.5±1.2; DZ 1 mg/kg=1.2±0.5, p<0.001).

Effect on DNF in the Horizontal Wire Test

Figure 8:
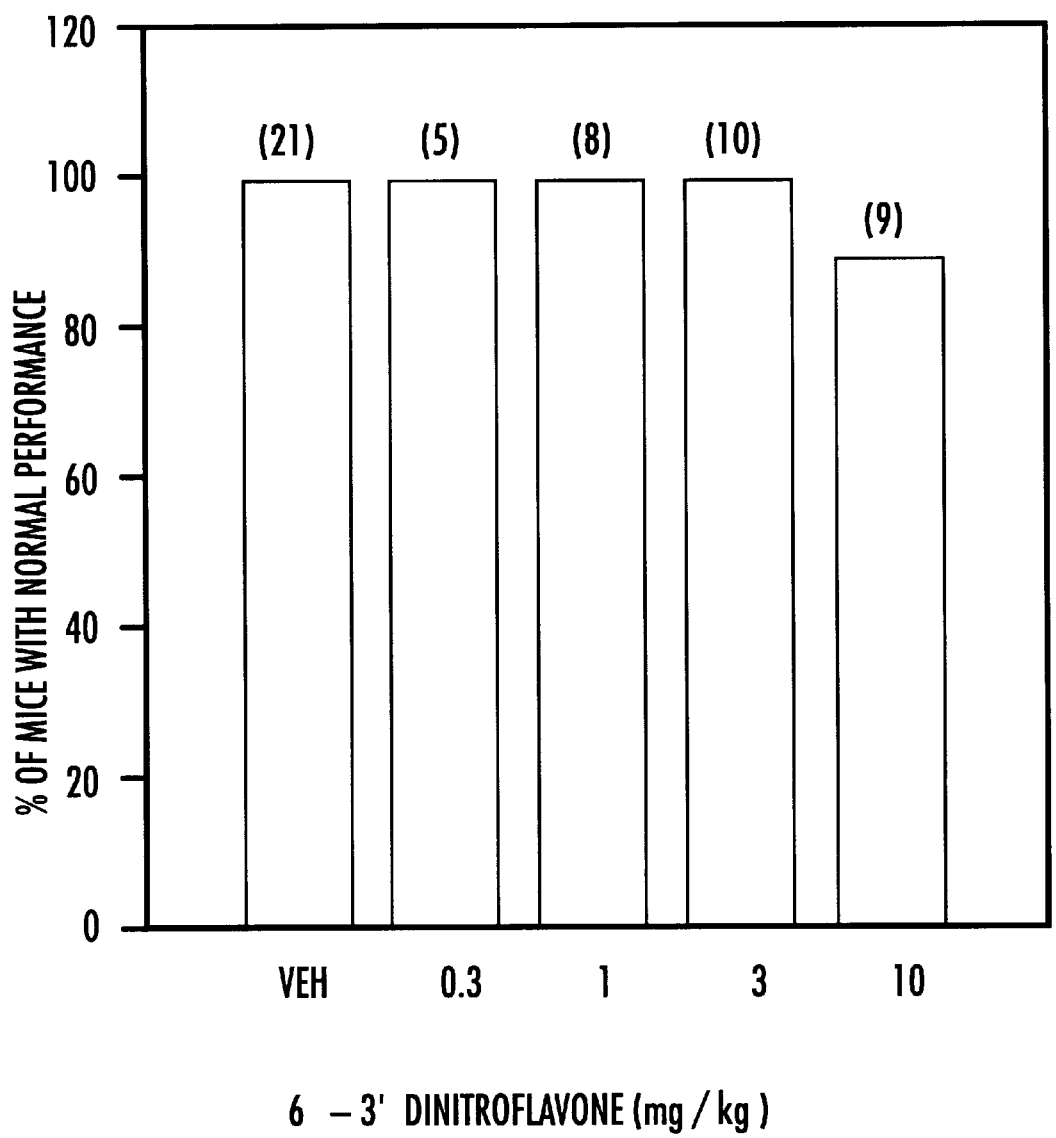
Figure 9:
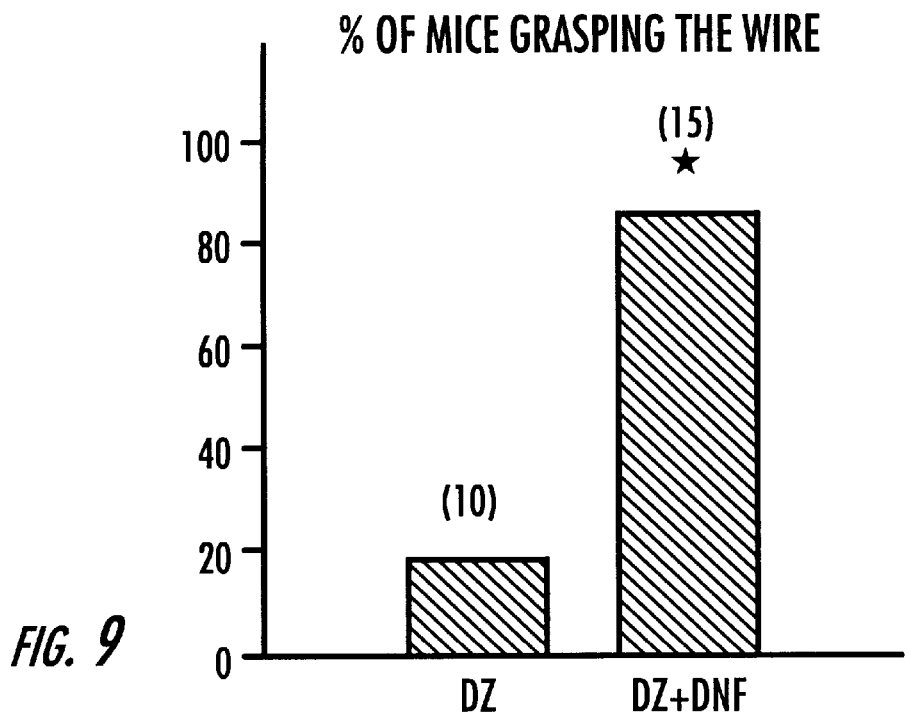

DNF, at doses up to 10 mg/kg, did not affect the percentage of mice grasping the wore (FIG. 8). On the other hand, the full central benzodiazepine receptor agonist DZ (1 mg/kg) produced a marked myorelaxant effect (8 animals out of 10) (FIG. 9). This myorelaxant action was counteracted by the administration of DNF plus DZ (1 mg/kg; 2 animals out of 15, p<0.001, $X^2$ test) (FIG. 9).

Effect of DNF on PTZ—Induced Convulsions

DNF, in a wide range of doses (30 μg/kg–6 mg/kg), did not prevent the seizures induced by 200 mg/kg PTZ in the mice (Table 3). In contrast, DZ (0.3–3 mg/kg) showed anticonvulsant activity (p<0.001, $X^2$ test) (Table 3).

TABLE 3

Effect of diazepam and 6,3'-dinitroflavone on pentylenetetrazole - induced seizures.

|  | $n^a$ | % of convulsing mice |
|---|---|---|
| VEH + PTZ | 25 | 96 |
| DZ 0.3 mg/kg | 6 | 33.3[b] |
| DZ 1.0 mg/kg | 12 | 42[b] |
| DZ 3.0 mg/kg | 9 | 0[b] |
| DNF 0.03 mg/kg | 6 | 100 |
| DNF 0.1 mg/kg | 12 | 75 |
| DNF 0.3 mg/kg | 15 | 80 |
| DNF 1.0 mg/kg | 13 | 92.4 |
| DNF 3.0 mg/kg | 5 | 100 |
| DNF 6.0 mg/kg | 7 | 100 |

Mice were i.p. injected with 200 mg/kg of pentylenetetrazole (PTZ) 15 min after an i.p. administration of vehicle (VEH), diazepam (DZ) or 6,3'-dinitroflavone (DNF). Data are expressed as the percentage of mice presenting clonic or tonic-clonic seizures. [a] number of animals per group.

[b]p<0.001, $X^2$test.

Effect on DNF on Thiopental—Induced Sleeping Time

As can be observed in Table 4, i.p. administration of 3 mg/kg DNF augmented the sleeping time (p<0.05). No changes were observed in latency to sleep. When injected at a lower dose (1 mg/kg) DNF did not change the latency or the sleeping time.

TABLE 4

Effect of 6,3'-dinitroflavone on thiopental-induced sleeping time.

|  | $n^a$ | Latency(s) | Sleeping Time(s) |
|---|---|---|---|
| VEH + TP | 16 | 233 (195/325) | 190 (11/478) |
| DNF 1 mg/kg + TP | 7 | 230 (164/300) | 207 (20/600) |
| DNF 3 mg/kg + TP | 12 | 237 (202/293) | 1277 (248/1800)* |

Mice were injected with sodium thiopental (TP, 22 mg/kg i.p.) 15 min after vehicle (VEH) or 6,3'-dinitroflavone (DNF). The ceiling of sleeping time was 1800 s. Data are expressed in medians (interquartile range). [a] number of animals per group.

*p<0.05, Dunn's multiple comparison test, after Kruskall Wallis (KW=6.93).

Effect of DNF on Inhibitory Avoidance and Tail Flick Tests

Figure 10:
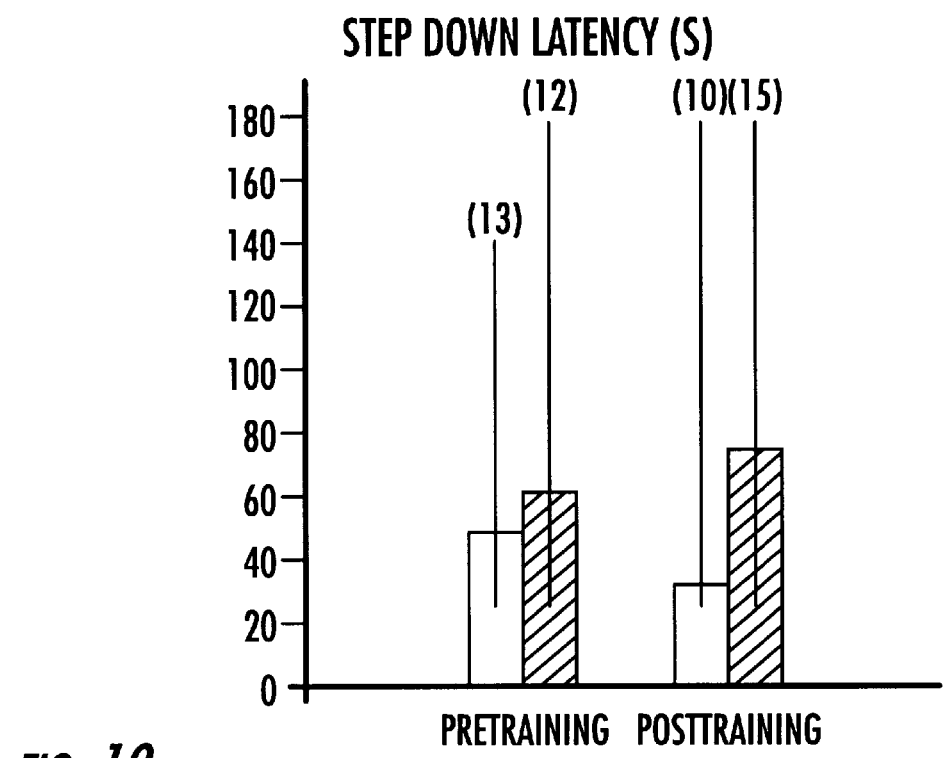

In rats, i.p. administration of 100 μg/kg DNF had no effect either pre or posttraining on the test session performance of inhibitory avoidance (FIG. 10). Furthermore, DNF at the same dose, did not alter TFL (Vehicle=3.2 s (2.8/4.3, n=11); DNF 100 μg/kg=3.5 s (2.7/4.2, n=11) [median (interquartile, p<0.05, Mann-Whitney U Test].

DISCUSSION

DNF has anxioselective properties and is thought to act at the central benzodiazepine receptor as a partial agonist with low selectivity for the central benzodiazepine receptor subtypes I and II.

Figure 4:
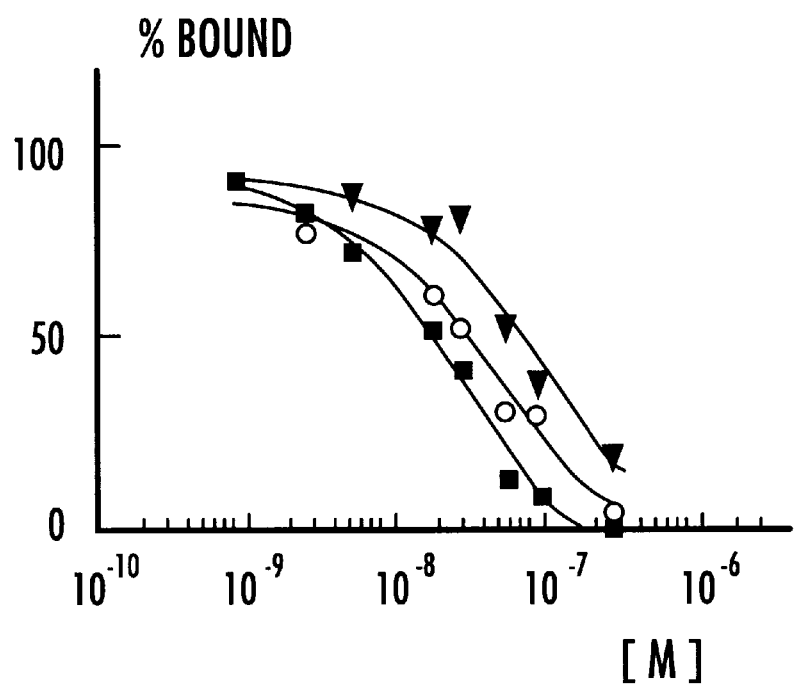

Pharmacological and biochemical evidence suggests the existence of these two distinct central benzodiazepine receptor types (Seigharth and Karobath, 1980; Trifiletti et al., 1984; Niddam et al., 1987; Mohler et al., 1995; McKernan and Whiting, 1996). The type I is the most abundant in the brain. The cerebellum is primarily enriched in this type (Niddam et al., 1987); the hippocampus (Arbilla et al., 1986) and cerebral cortex contain mixed amounts of types I and II (Trifiletti et al, 1984 ), whereas type II is predominant in a few brain areas such as striatum, spinal cord, dentate gyrus and olfactory bulb (Watanabe et al., 1985; Niddam et al., 1987; Pritchett et al., 1989; McKernan and Whiting, 1986). Using crude synaptosomal membranes (FIG. 3 and Table 2), we found the lowest DNF inhibition constants for [$^3$H]—FNZ binding in cerebellum, followed by cerebral cortex>hippocampus>striatum~spinal cord. In autoradiographic experiments the rank order of potency was cerebellum>parietal cortex>striatum>dentate gyrus (FIG. 4). These findings could be due to different affinities of DNF for the central benzodiazepine receptor subtypes and their relative densities in each brain region. In those areas with mixed populations of subtypes I and II (e.g. cerebral cortex and hippocampus) the resultant $K_i$ values may reflect the average affinity for central benzodiazepine receptor types I and II. In contrast, we found two well-defined binding sites in cortical membranes using the preferentially central benzodiazepine receptor type I agonist CL 218,872 (high affinity $K_i$ value=10 nM low affinity $K_i$ value=1.2 μM). In addition, using a selective central benzodiazepine receptor I ligand, [$^3$H]—ZOLP (Arbilla et al., 1986), DNF had similar $K_i$ values for cerebral cortex, striatum and cerebellum. These affinities are concordant with the nature of the cerebellar binding site. DNF is a selective ligand for the central benzodiazepine receptors because it did not displace the binding of specific [$^3$H] radioligands to α1 and β adrenergic, muscarinic cholinergic, $GABA_A$ or $5-HT_{IA}$ receptors.

Confirming and expanding recent findings indicating that very low doses of DNF (1–30 μg/kg) have a potent anxiolytic action as measured in the elevated plus maze, the DNF-induced increase in open arms exploration observed in the present study was blocked by the administration of the selective benzodiazepine antagonist Ro 15-1788 (FIG. 6). DNF (up to 10 mg/kg) did not evidence anticonvulsant, myorelaxant, amnesic or analgesic effects (Table 3 and FIGS. 8 and 10).

On the other hand, DNF possesses a slight depressant action at high doses (100–300 times higher than those producing anxiolytic effects) as evidenced by the thiopental sleeping time potentiation (Table 4) and by both a reduction in the locomotor ambulatory activity and a decrease in holeboard exploration (FIGS. 5 and 7) (File 1985). Therefore, DNF can reduce anxiety at doses well below those causing sedation.

In comparison to DZ, DNF is a 30 times more potent anxiolytic and required a 10 fold higher dose to produce similar sedative effects.

We demonstrated that DNF was able to reverse the myorelaxant effect of the full agonist DZ (FIG. 9).

Due to its selective pharmacological profile and low intrinsic efficacy, and its potentiality to induce less unwanted side effects, DNF may represent an improved therapeutic tool for the treatment of anxiety.

In conclusion, DNF is a specific and high affinity benzodiazepine receptor ligand that exhibits mild regional differences in its potency to displace [$^3$H]—FNZ binding to central benzodiazepine receptors. It has an anxioselective action in mice and prevents the muscle relaxation effect of a full benzodiazepine receptor agonist.

EXAMPLES SECTION 3: 6-BROMO-3'-NITROFLAVONE AND FURTHER NITROFLAVONES 6-bromo-3'-nitroflavone (IV), 6-bromo-2'-nitroflavone (III) and 6-bromo-4'-nitroflavone (V) were prepared as follows:

Method A

Compounds IV, V and III were prepared in two steps staring with flavanone (1) (Extrasynthese, France) as indicated in Scheme 1.

To a solution of (1) (2.7 mmol) and pyridine (0.15 mmol) in C Cl$_4$ (9.6 mL), at 0° C., a solution of bromine (6.2 mmol) in C Cl$_4$ (3.72 mL) was added dropwise. The mixture was stirred for 1 h at 30° C. followed by 45 min at 65° C. After cooling, the reaction mixture was washed with two 100 mL portions of a saturated aqueous solution of Na$_2$S$_3$O$_5$ and then with water, dried over Na$_2$SO$_2$ and concentrated to dryness in a rotary evaporator.

The crude product dissolved in toluene was chromatographed in a column (2.5 cm×40 cm) of silica gel, 10–40 μ, type H, eluted stepwise with 200 mL of toluene, followed by equal volumes of toluene containing 1, 2, 3, 4 and 5% acetone (V/V).

The fractions obtained were pooled according to the results of their analysis by TLC. The pool containing 6 bromoflavone (2) was recovered by evaporation of the solvent and recrystallised from ethanol-water.

Compound (2):6 bromoflavone mp:189–190° C. UV λ$_{max}$ 256, 299 nm. EIMS M$^+$ 300 and 302 (C$_{15}$H$_9$O$_2$Br). $^1$H NMR (DMSO-d$_0$, 400 MHz) δ 8.11–8.13 (3 H, m, H-5, H-2', H-6'), 8.00 (1 H, dd, J=8, 2 Hz, H-7), 7.47 (1 H, d, J=8 Hz, H-8), 7.57–7.63 (3 H, m, H-3', H-4', H-5'), 7.11 (1 H, s, H-3). $^{-C\ NMR}$ (100 MHz) 162.9 (s, C-2), 106.9 (d, C-3), 175.9 (s, C-4), 124.9 (s, C-4a), 126.9 (d, C-5), 117.9 (s, C-6), 136.9 (d, C-7), 121.3 (d, C-8), 154.7 (s, C-8a), (s, C-1'), 126.5 (C-2'/C-6'), 129.1 (C-3'/C-5'), 132.0 (C-4').

Compound (2) was dissolved in anhydrous nitric acid at 0° C. The resulting solution was allowed to stand 45 min at room temperature and then an excess of water was added, with stirring. The precipitate collected by filtration, was dissolved in toluene and chromatographed, as indicated before, in a column of silica gel: three fractions were obtain. They were recovered by evaporation of the solvent, purified by recrystallisation from acetone-water. The compounds obtained were identified by $^1$H NMR as those numbered IV, V and III in Scheme 1.

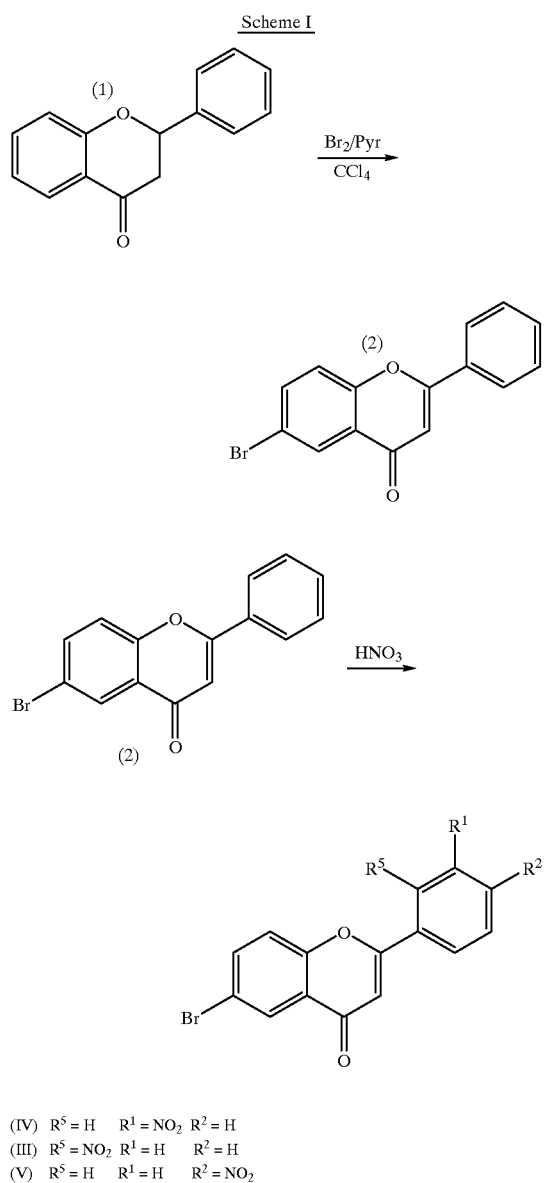

Scheme I (IV) R$^5$ = H  R$^1$ = NO$_2$  R$^2$ = H
(III) R$^5$ = NO$_2$  R$^1$ = H  R$^2$ = H
(V) R$^5$ = H  R$^1$ = H  R$^2$ = NO$_2$ The three compounds gave MS and elemental analytical data consistent with their structures. Compound (IV): $^1$H NMR (300 Mhz, CDCl$_3$): δ 8.80 (t, J=2.0 Hz, H-2'), 8.42 (dt, J=8.0, 2.4 Hz, H-4'), 8.37 (d, J=2.4 Hz, H-5'), 8.21 (dt, J=8.0, 2.0 Hz, H-6'), 7.84 (dd, J=8.8, 2.5 Hz, H-7'), 7.76 (t, J=8.2 Hz, H-5'), 7.54 (d, J=9.2 Hz, H-8'), 6.92 (s, H-3').

Compound (V); $^1$H NMR (300 Mhz, CDCl$_3$)', H-6'), 8.10 (d, J=8.8 Hz, H-3', H-5'), 7.84 (dd, J=9.0, 2.4 Hz, H-7), 7.52 (d, J=9.0 Hz, H-8), 6.92 (s, H-3).

Compound (III): $^1$H NMR (300 Mhz, CDCl$_3$): δ 8.37 (d, J=2.4 Hz, H-5), 8.11 (dd, J=1.5, 7.7 Hz, H-6'), 7.75 (m, H-7, H-3', H-4', H-5'), 7.29 (d, J=9.0 Hz, H-8), 6.60 (s, H-3).

The 6,3' dinitroflavones of the invention may also be synthesised according to the teaching of Ares J. J. et al. J. Med. Chem (1995) 38, pp. 4937–4943 (method B) modified as outlined below:

Scheme II

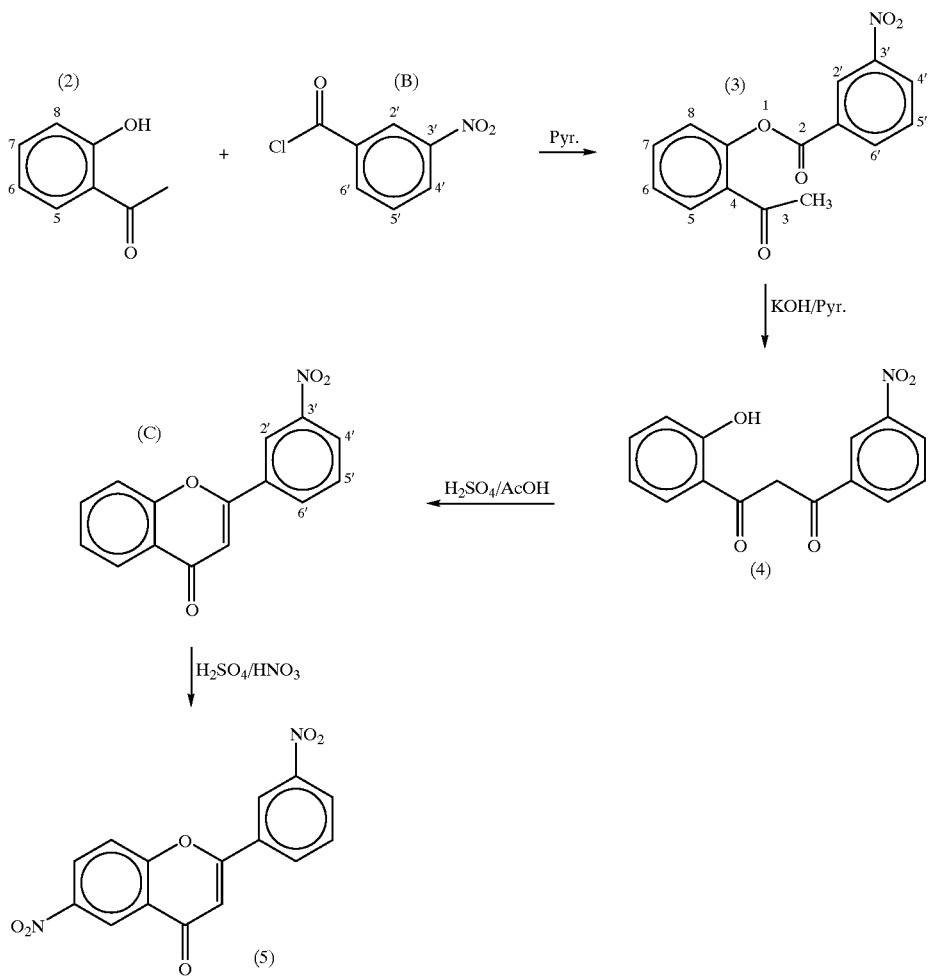

For the purposes of the present invention, the ring numbering system of Scheme II is used for reasons of consistency with respect to the numbering system of Formula (I).

Naturally, the man skilled in the art will appreciate that other nitroflavones of the invention may be synthesised following the outline above when the benzoyl halide (B) comprises one or more nitro groups located at other positions on the aromatic ring to the 3' position shown above, such as at positions 2', 4', 5' and/or 6' of the benzoyl halide. Suitable benzoyl halides include benzoyl chloride, benzoyl bromide or benzoyl fluoride having the nitro group located at the 3' position or other benzoyl halides wherein the nitro group is positioned at other positions on the aromatic ring, for example, at the 2' and/or 4' positions thereon.

The man skilled in the art will also appreciate that halo nitroflavones of the invention may be synthesised following the general outline provided above prior to the nitration step of the flavone nucleus, starting with a suitably halogenated 2-hydroxyacetophenone which may then be reacted with a suitable benzoyl halide as described above. Halo groups may be positioned on the acetophenone at one or more of the free carbon positions of the aromatic ring, such as at the 5, 6, 7, and/or 8 positions shown above. The halo substituent on the aromatic ring of the acetophenone may be selected from Cl, Br, or F and is preferably located at the 6 position of the aromatic ring of the said acetophenone.

In cases wherein nitroflavones of the invention (e.g. compounds VI and VII) do not possess halo or nitro groups on the flavone nucleus, the general synthetic process for producing such nitroflavones may comprise reacting a 2-hydroxyacetophenone comprising H substituents on the aromatic ring at positions 5, 6, 7 and 8 thereof with an appropriate benzoyl halide and following the general outline above to compound (C). Naturally, the man skilled in the art will appreciate that nitro groups may be located on the 3', 4', 5' or 6' position of the phenyl ring of such nitroflavones depending on the design.

To obtain dinitroflavone derivatives with a $NO_2$ group at position 6, compound (C) comprising H substituents at all free carbon positions of the flavone nucleus and appropriate $NO_2$ substituent on the phenyl ring thereof may be nitrated according to the teaching of Cushman M. et al. J. Med Chem. (1994) 37, pp. 3353–3362.

Specific compounds of the invention i.e. compounds (II) to (IX) inclusive may be prepared as follows:

(1) Compounds 6,3'-dinitroflavone (II) and 3' nitroflavone (VI)

Reference is made to Scheme II.

Step 1

1 To a solution of the acid chloride (B) (Aldrich) (15 mmol) in pyridine (10 ml), at 0° C., solid 2-hydroxyacetophenone (2) (9 mmol) was added with stirring. The reaction mixture was stirred for 15 minutes at 0° C. followed by 30 minutes at room temperature. Then it was poured into a 3% aqueous HCl/ice solution with vigorous stirring. The resulting precipitate was filtered and washed with water. The crude material was recrystallized from methanol yielding compound (3) (75% yield).

Step 2

To a solution of (3) (10 mmol) in pyridine (10 ml), at 50° C., pulverized potassium hydroxide (15 mmol) was added. The mixture was stirred for 15 minutes and, after cooling, at 10% aqueous acetic acid solution was added. The resulting precipitate was filtered. The crude material, containing the diketone (4), was used in the next step without purification.

Step 3

A mixture of the crude material from step 2 (equivalent to 10 mmol of compound (4), with concentrated sulfuric acid (0.5 ml), and glacial acetic acid (13 ml) was heated at reflux for 1 hour and cooled to room temperature. Then, the mixture was poured onto crushed ice (75 g), and the resulting precipitate was filtered.

Recrystallisation from acetone afforded product (C), 3'-nitroflavone (VI) (mp. 205.2–205.7° C.) (65% yield).

Step 4 to a mixture of (C) (5 mmol) in concentrated sulfuric acid (14 ml), at room temperature, nitric acid (d=1.40, 1.6 ml) was added with stirring. The reaction was allowed to proceed for 3 hours, and the mixture was then poured onto ice (100 g). The precipitated product was filtered, washed with water, and dried. Recrystallisation from acetone afforded (5), 6,3'-dinitroflavone (II) (mp. 290–292° C., yield 90%; NMR data provided on page 20 herein).

3'-Nitroflavone (VI): $^1$H—NMR (200 Mhz, CDCl$_3$): δ 8.83 (t, J=1.8 Hz, H-2'), 8.56 (d, J=8.1 Hz, H-4'), 8.42 (dd, J=2.0 Hz, 8.1 Hz, H-5), 8.07 (d, J=8.0 Hz, H-6'), 7.88 (m, H-7, H-8), 7.53 (m, H-6), 7.28 (s, H-3).

(2) 6-bromo-3'-nitroflavone (IV)

Steps 1, 2 and 3, same conditions, (Scheme II) but using compounds 6 (Aldrich) and (B) as starting materials.

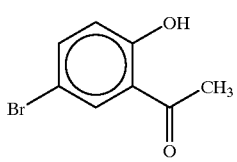
(6)

[NMR data provided on page 39 herein]

(3) 6-bromo-2'-nitroflavone (III)

Steps 1, 2 and 3, same conditions (Scheme II) but using compounds 6 and 7 (Aldrich) as starting materials.

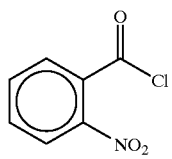
(7)

[NMR data provided on page 40 herein]

(4) 6-bromo-4'-nitroflavone (V)

Steps 1, 2 and 3, same conditions (Scheme II) but using compounds 6 and 8 (Aldrich) as starting materials.

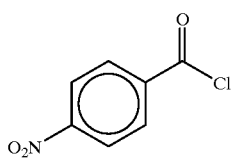
(8)

[NMR data provided on page 40 herein]

(5) 4'-nitroflavone (VII)

Steps 1, 2 and 3, same conditions (Scheme II) but using compounds 2 and 8 (Aldrich) as starting materials.

4'-Nitroflavone (VII): $^1$H—NMR (300 Mhz, CDCl$_3$), δ 8.40 (d, J=8.80 Hz, H-2', H-6'), 8.25 (dd, J=1.60 Hz, 8.0 Hz, H-5), 8.12 (d, J=8.80 Hz, H-3', H-5') 7.77 (td, J=2.0 Hz, 7.20 Hz, H-7), 7.62 (dd, J=1.60 Hz, 8.60 Hz, H-8), 7.47 (td, J=1.0 Hz, 8.0 Hz, H-6), 6.92 (s, H-3).

(6) 6-Chloro-3'-nitroflavone (VIII)

Steps 1, 2 and 3, same conditions (Scheme II) but using compounds 1 and 9 (Aldrich) as starting materials.

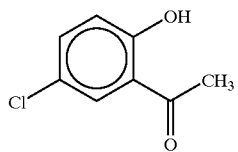
(9)

6-chloro-3'-nitroflavone (VIII): $^1$H—NMR (200 Mhz, CDCl$_3$) δ 8.80 (s, H-2'), 8.41 (d, J=2.5 Hz, H-5), 8.21 (m, H-4', H-6'), 7.75 (t, J=8.2 Mz, H-5'), 7.70 (dd, J=8.7 Hz, 2.4 Hz, H-7), 7.60 (d, J=9.0 Hz, H-8), 6.90 (s, H-3).

(7) 6-Fluoro-3'-nitroflavone (IX)

Steps 1, 2 and 3, same conditions (Scheme II) but using compounds 1 and 10 (Aldrich) as starting materials.

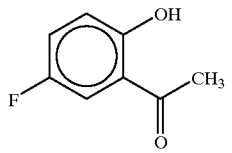
(10)

6-Fluoro-3'-nitroflavone (IX): $^1$H—NMR (200 Mhz, CDl$_3$) δ 8.82 (t, J=2 Hz, H-2'), 8.44 (dt, J=2.1 Hz, 8.2 Hz, H-4'), 8.25 (dt, J=2.2 Hz, 8.3 Hz, H-3'), 7.90 (dd, J=3.2 Hz, 8.3 Hz, H-8), 7.80 (t, J=8.1 Hz, H-5'), 7.65 (dd, J=3.3 Hz, 8.2 Hz, H-5), 7.52 (m, H-7), 6.91 (s, H-3).

(i) Binding to Central Benzodiazepine Receptors (BDZ—Rs) of Rat Membranes (Compound IV).

The binding of $^3$H—FNZ (81.8 Ci/mmol; NEN) (FIG. 11) was carried out as described by Levi de Stein, M. et al., *Mol. Brain Res.* 1989, 5, 9. In brief, for each assay, triplicate samples of the membranes, containing 0.2 to 0.4 mg protein were suspended in a final volume of 1 mL of 0.25 mM Tris—HCl buffer, pH 7.3. The incubation was carried out at 4° C. for 60 min with 0.6 nM $^3$H—FNZ. to study the binding saturation, a range of 0.3 to 10 nM $^3$H—FNZ was used. Non-specific binding was determined in parallel incubations in the presence of 3 μM FNZ, and represented 5–15% of total. The assays were terminated by filtration under vacuum through Whatman GF/A glass-fiber filters, and three washes with 3 mL each of incubation medium. Filters were dried and counted after the addition of 5 mL of 2,5-diphenyloxazole/xylene as scintillation fluid.

(ii) Binding to BDZ—R's of Rat Cerebral Cortex Membranes (Compounds II, III, V, VI, VII, VIII, and IX).

The binding of $^3$H—FNZ was carried out as for (i) above. Results are shown in Table 5 below.

TABLE 5

Effect of Compounds II, III, V, VI, VII, VIII and IX on $^3$H-FNZ Binding to Synaptosomal Membranes from Rat Cerebral Cortex.

| Compound | Ki nM |
|---|---|
| II | 20 |
| III | 208 |
| V | 220 |
| VI | 250 |
| VII | 300 |
| VIII | 8 |
| IX | 170 |

(iii) Elevated Plus-Maze

The animals used in the pharmacological test were male Swiss mice from our breeding stock, weighting 28–35 g. They were placed in groups of ten with free access to water and food, and maintained on 12 h/12 h day/night cycle. The elevated plus-maze set-up consisted of a maze of two open arms, 25×5 cm, crossed by two closed arms of the same dimensions, with free access to all arms from the crossing point. The closed arms had walls 35 cm high all around. The maze was suspended 50 cm from the room floor. Mice were placed on the central part of the cross facing an open arm. The number of entries and the time spend going into open and closed arms were counted during 5 min. A selective increase in the parameters corresponding to open arms revels an anxiolytic effect. The total exploratory activity (number of entries in both arms) was also determined according to the method of Pellow, S. J. et al. *Neurosci. Meth.* 1986, 14, 149; Lister, R. G. *Psychopharmacology* 1987, 92, 180).

RESULTS AND DISCUSSION

Figure 11:
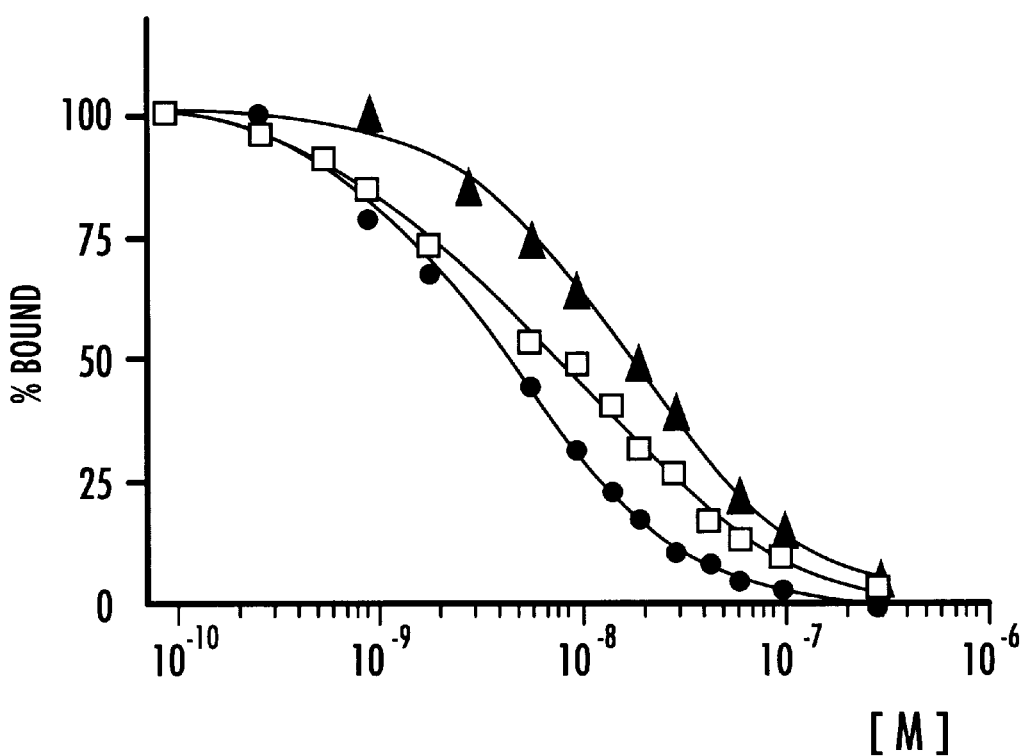

Non-specific nitration of compound 6-bromoflavone yielded three major products. Compounds (III) and (IV) inhibited the binding of $^3$H—FNZ to extensively washed rat cerebral cortical membranes with $K_i$ of 208±19 nM (n=4) and 220±1 nM (n=2) (Table 5), respectively, but compound (IV) was several times more active, as shown in Table 6. The potency of compound (IV) in displacing $^3$H—FNZ binding was highest in the cerebellum and in one population of cerebral cortical BDZ binding sites (FIG. 11). In the brain regions were the type II BDZ—R predominates, compound (IV) exhibits a potency for displacement of $^3$—FNZ binding 3–4 times lower than that found for the cerebellum, a region of the brain that has an homogeneous population of type I BDZ—Rs (*Siegharth, W. Trends Pharmacol. Sci.* (1992), 13 P. 446; *Doble, A. and Martin I. L. Trends Pharmacol. Sci.* (1992) 13, p. 76). In addition, in the spinal cord compound (IV) has an affinity 10 times lower than the highest value found in the cerebral cortex, where it recognises two distinct populations of binding sites with $K_{1,5}$ of 1.2 nM and 15.5 nM, respectively (Table 6 and FIG. 11).

TABLE 6

Effect of compound IV on $^3$H-FNZ binding to synaptosmal membranes from several brain structures (see FIG. 11).

| STRUCTURE | n | K$_i$SEM (nM) |
|---|---|---|
| cerebellum | 4 | 3.6 ± 0.1 |
| hippocampus | 2 | 9.6 ± 0.6 |
| striatum | 3 | 9.8 ± 1.6 |
| spinal cord | 3 | 12.7 ± 0.5 |
| cerebral cortex | 6 | 1.2 ± 0.4 & 15.5 ± 0.9 |

Scatchard analysis of saturation curves of $^3$H-FNZ binding to cerebral cortical membranes reveals that compound (IV) is a competitive ligand for the BDZ-R (data not shown).

On the other hand, in the cerebellum and the cerebral cortex, compound (IV) displaces $^3$H-zolpidem with similar potencies (3±1 nM and 3.8±1 nM, n=3, respectively). Zolpidem is an imidazopyridine possessing selectivity for the type I BDZ-Rs (Arbilla S. et al supra).

Compound (IV) appears to be a selective BDZ-R ligand because it does not displace (at 10 $\mu$M) $^3$H-muscimol, $^3$H-AMPA, $^3$H-QNB, and $^3$H-8-OH-DPAT bindings for GABA$_A$, AMPA-glutamate, cholinergic-muscarinic and serotonin 1$_A$ receptors, respectively.

Figure 12:
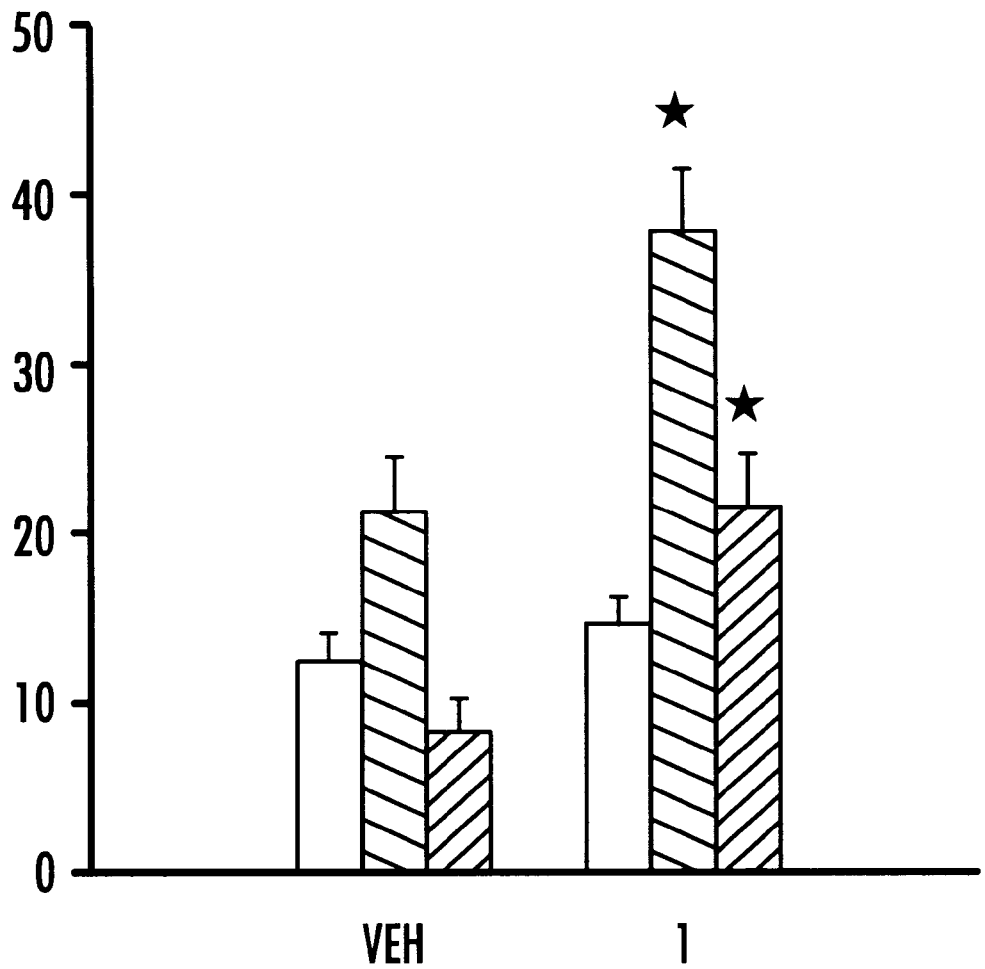

Preliminary pharmacological experiments in mice reveal that compound (IV) at 0.1 mg/kg, i.p. has anxiolytic properties in the elevated plus-maze, increasing both the percentage of entries in the open arms and the time spent in these arms (FIG. 12).

In conclusion, we have presented evidence that compound (IV) is a high affinity BDZ-R ligand with agonistic properties, which recognises two populations of binding sites in the cerebral cortex and displays a differential potency for the inhibition of $^3$H-FNZ binding in several regions of the rat brain, in accordance with the regional distribution of type I BDZ-R.

References

Anca, J. M., M. Lamela, M. A. Gato, I. Cadavid and J. M. Calleja, 1992, Activity on the central nervous system of *Himanthalia elongata,* part II, Planta Med. 59, 101.

Arbilla, S., J. Allen, A. Wick and S. Z. Langer, 1986, High affinity ($^3$H) zolpidem binding in the rat brain: an imidazopyridine with agonist properties at central benzodiazepine receptors, Eur. J. Pharmacol. 130, 257.

Bernabeu, R., I. Izquierdo, D. Jerusalinsky, M. Cammarota and J. H. Medina, 1995, Learning-specific, time-dependent increase in [$^3$H] phorbol dibutyrate binding to PKC in selective regions of the rat brain, Brain Res. 685–163.

Bonetti, E. P., L. Pierri, R. Cumin, M. Schaffner, E. R. Gamzu, R. K. M. Muller and W. Haefelu, 1982. Benzodiazepine antagonist RO 15-1788: neurological and behavioral effects, Psychopharmacol. 78, 8.

Cammarota, M., C. Wolfman, D. Jerusalinsky, R. Bernabeu, M. Levi de Stein, I. Izquierdo and J. H. Medina, 1995, Inhibitory avoidance training-induced selective changes in [$^3$H] AMPA receptor binding in the hippocampal formation, Neurobiol. Learn. & Mem. 64, 257.

Dawson, G. R. and M. D. Tricklebank, 1995, Use of the elevated plus maze in the search for novel anxiolytic agents, TIPS 16, 33.

Doble, A. and Martin I. L. Trends Pharmacol. Sci. (1992) 13, p. 76.

File, S. E., 1985, What can be learned from the effects of benzodiazepines on exploratory behaviour? Biobehav. Rev. 9, 45.

File, S. E., and S. Pellow, 1985, The effects of triazolobenzodiazepines in two animal tests of anxiety and in the holeboard, Brit. J. Pharmacol. 86, 729.

File, S. E. and S. Pellow, 1986, Intrinsic actions of the benzodiazepine receptor antagonist RO 15-1788, Psychopharmacol. 88, 1.

Izquierdo, I., C. Da Cunha, C. Huang, R. Walz, C. Wolfman and J. H. Medina, 1990, Posttraining down-regulation of memory consolidation by a $GABA_A$ mechanism in the amygdala modulated by endogenous benzodiazepine, Behav. Neural Biol. 54, 105.

Jerusalinsky, D., J. H. Medina and E. De Robertis, 1983, Lesion of the forebrain nuclei reveals possible presynaptic cholinergic muscarinic receptors in the rat cerebral cortex, Neuropharmacol. 22, 835.

Lister R. G., 1987, The use of a plus maze to measure anxiety in the mouse, Psychopharmacol. 92, 180.

Lowry, O. H., N. J. Rosebrough, A. L. Farr and R. Randall, 1951, Protein measurement with the Folin phenol reagent, J. Biol. Chem. 193, 265.

McKernan, R. M. and P. J. Whiting, 1996, Which $GABA_A$ receptors subtypes really occur in the brain? TINS 19, 139.

Medina, J. H., M. L. Novas and E. De Robertis, 1983, Changes in benzodiazepine receptors by acute stress: different effects of chronic diazepam or Ro 15-1788 treatment, Eur. J. Pharmacol. 96, 181.

Medina, J. H., C. Wolfman, M. Levi de Stein, O. Tumilasci and A. B. Houssay, 1984, Thyroid hormone regulation of adrenergic receptors and β-adrenergic responsiveness on the submandibular gland, Life Sci. 35, 819.

Medina, J. H., A. C. Paladini, C. Wolfman, M. Levi de Stein, D. Calvo, L. Diaz and C. Peña, 1990, Chrysin (5–7 di OH flavone), a naturally-occurring ligand for benzodiazepine receptors with anticonvulsant properties, Biochem. Pharmacol. 40, 2227.

Mohler H., F. Knoflach, J. Paysan, K. Motejlek, D. Benke, B. Lüscher and J. M. Fritschy, 1995, Heterogeneity of $GABA_A$ receptors: cell-specific expression, pharmacology, and regulation, Neurochem. Res. 20, 631.

Nénonéné E. K., F. Radja, M. Carli, L. Grondin and T. A. Reader, 1994, Heterogeneity of cortical and hippocampal $5-HT_{1A}$ receptors: a reappraisal of homogenate binding with 8-[$^3$H] hydroxydipropylaminotetralin, J. Neurochem. 62, 1822.

Niddam, R., A. Dubois, B. Scatton, S. Arbilla and S. Z. Langer, 1987, Autoradiographic localisation of [$^3$H] zolpidem binding sites in the rat CNS: comparison with the distribution of [$^3$H] flunitrazepam binding sites, J. Neurochem. 49, 890.

Pellow, S. and S. File, 1986, Anxiolytic and anxiogenic drug effects an exploratory activity in an elevated plus maze. A novel test of anxiety in the rat, Pharmacol. Biochem. Behav. 24, 525.

Pellow, S., P. Chopin, S. File and M. Briley, 1985, Validation of open:closed arm entries in an elevated plus maze as measure of anxiety in the rat, J. Neurosci. Meth., 14, 149.

Potokar, J. and D. J. Nutt, 1994, Anxiolytic potential of benzodiazepine receptor partial agonists, CNS Drugs 1, 305.

Pritchett, D. B., H. Lüddens, P. H. Seeburg, 1989, Type I and type II $GABA_A$ benzodiazepine receptors produced in transfected cells, Science 245, 1389.

Siegfried B., C. Netto and I. Izquierdo, 1987, Exposure to novelty induces naltrexone-reversible analgesia in rats, Behav. Neurosci. 101, 436.

Sigharth, W. 1992, Trends Pharmacol. Sci. 13, p. 76.

Siegharth W. and M. Karobath, 1980, Molecular heterogeneity of benzodiazepine receptors Nature (Lond.) 285, 826.

Tifiletti R. R., M. M. S. Lo and S. H. Snyder, 1984, Kinetic differences between type I and type II benzodiazepine receptors, Mol. Pharmacol. 26, 228.

Viola, H., C. Wolfman, M. Levi de Stein, C. Wasowski, C. Peña, J. H. Medina and A. C. Paldini, 1994, Isolation of pharmacologically active benzodiazepine receptor ligand from *Tilia tomentosa*, J. Etnopharmacol. 44, 47.

Viola, H., C. Wasowski, M. Levi de Stein, C. Wolfman, R. Silveira, F. Dajas, J. H. Medina and A. C. Paladini, 1995, Apigenin, a component of *Matricaria recutita* flowers, is a central benzodiazepine receptors-ligand with anxiolytic effects, Plant Med. 61, 213.

Watanabe, Y., S. Katami, T. Shibuya and B. Salafsky., 1985, Ontogenetic properties of benzodiazepine receptor subtypes in rat spinal cord, Eur. J. Pharmacol. 109, 307.

Wolfman, C., H. Viola, A. C. Paladini, F. Dajas and J. H. Medina, 1994, Possible anxiolytic effects of chrysin, a central benzodiazepine receptor ligand isolated from *Passiflora coerulea*, Pharmacol. Biochem. Behav. 47, 1.

What is claimed is:

1. A method of treating anxiety in a patient which comprises administering to the patient an effective non-toxic amount of a flavonoid of general formula (I):

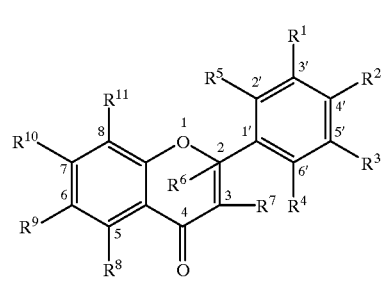

wherein $R^1$, $R^2$, $R^3$, $R^4$ and $R^5$ are independently selected from $NO_2$ and H;

$R^6$ and $R^7$ are independently selected from Br, Cl, F, and H or $R^6$ and $R^7$ together form a single bond;

$R^8$, $R^{10}$ and $R^{11}$ are independently selected from H, —OH, —R, —$NO_2$, Br, Cl, F, —OR, —$NH_2$, —NHR, —$NR_2$, —COOR, —COOH, —CN or a sugar group;

$R^9$ is selected from H, $NO_2$, Br, Cl, or F;

R is $C_1$–$C_6$ alkyl or alkenyl;

with the proviso that at least one of $R^1$, $R^2$, $R^3$, $R^4$ and $R^5$ is $NO_2$ and with the exception that when $R^9$ is H, $R^5$ is H, or the administration of an effective non-toxic amount of a bi-flavonoid which is a dimer of a compound of general formula (I).

2. A method according to claim 1 wherein $R^1$, $R^2$ and $R^5$ are independently selected from $NO_3$ and H;

$R^8$, $R^{10}$ and $R^{11}$ are all hydrogen;

$R^9$ is selected from H, $NO_2$, Br, Cl, or F;

with the proviso that at least one of $R^1$, $R^2$ and $R^5$ is $NO_2$, with the exception that when $R^9$ is H, $R^5$ is H.

3. A method according to claim 1 wherein $R^1$, $R^2$ and $R^5$ are independently selected from H and $NO_2$;

$R^6$ and $R^7$ together form a single bond;

$R^9$ is selected from H, $NO_2$, Br, Cl, or F; with the proviso that at least one of $R^1$, $R^2$ and $R^5$ is $NO_2$ with the exception that when $R^9$ is H, $R^5$ is H.

4. A method according to claim 1 wherein $R^1$, $R^2$ and $R^5$ are independently selected from $NO_2$ and H;

$R^3$, $R^4$, $R^8$, $R^{10}$ and $R^{11}$ are all H;

$R^6$ and $R^7$ together form a single bond;

$R^9$ is selected from Br, Cl, F and $NO_2$;

with the proviso that at least one of $R^1$, $R^2$ and $R^5$ is $NO_2$.

5. A method according to claim 1 wherein the compound is:

(II)

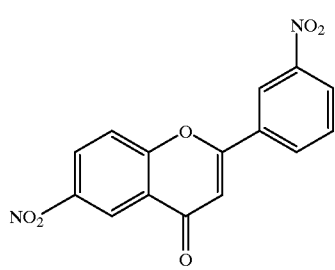

6. A method according to claim 1 wherein the compound is:

(III)

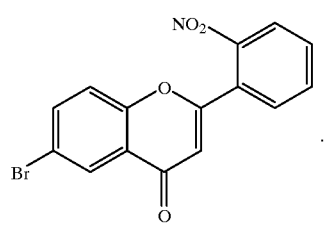

7. A method according to claim 1 wherein the compound is:

(IV)

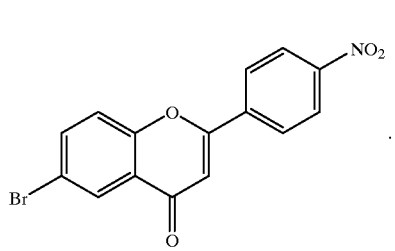

8. A method according to claim 1 wherein the compound is:

(V)

9. A method according to claim 1 wherein the compound is:

(VI)

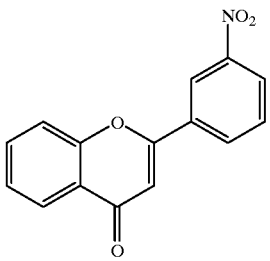

10. A method according to claim 1 wherein the compound is:

(VII)

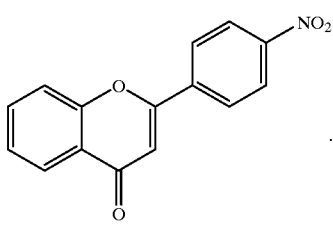

11. A method according to claim 1 wherein the compound is:

(VIII)

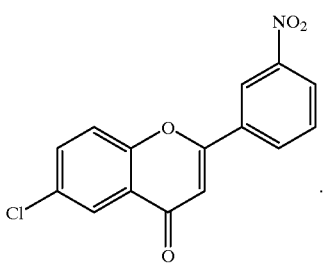

12. A method according to claim 1 wherein the compound is:

(IX)

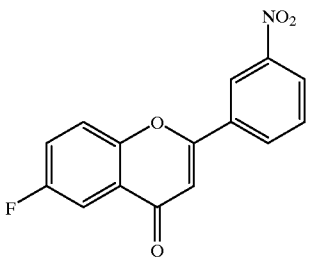

13. A method according to claim 1 wherein the bi-flavonoid dimer has the general formula (X):

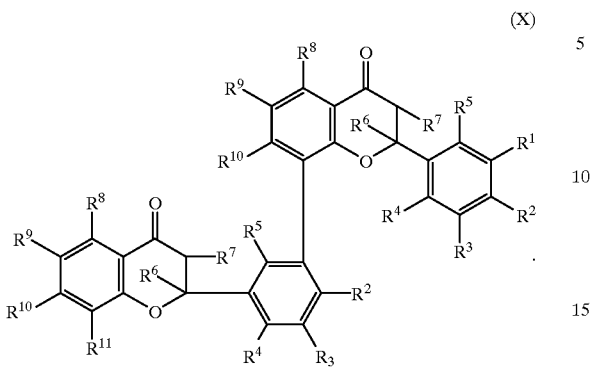

wherein $R^1$ to $R^{11}$ have the same definitions given in claim 1.

14. A method according to claim 13 wherein $R^1$, $R^2$ and $R^5$ are independently selected from $NO_2$ and H;

$R^9$ is selected from H, $NO_2$, Br, Cl and F; with the proviso that at least one of $R^1$, $R^2$ and $R^5$ is $NO_2$ and with the exception that when $R^9$ is H, $R^5$ is H.

15. A method according to claim 13 wherein $R^1$, $R^2$ and $R^5$ are independently selected from H and $NO_2$;

$R^6$ and $R^7$ together form a single bond;

$R^9$ is selected from H, $NO_2$, Br, Cl and F; with the proviso that at least one of $R^1$, $R^2$ and $R^5$ is $NO_2$ and with the exception that when $R^9$ is H, $R^5$ is H.

16. A method according to claim 13 wherein $R^1$, $R^2$ and $R^5$ are independently selected from $NO_2$ and H;

$R^3$, $R^4$, $R^8$, $R^{10}$, and $R^{11}$ are all H;

$R^6$ and $R^7$ together form a single bond;

$R^9$ is selected from Br, Cl and F and $NO_2$;

with the proviso that at least one of $R^1$, $R^2$ and $R^5$ is $NO_2$.

17. A method according to claim 1 or 13 wherein the treatment reduces anxiety without exerting a substantially sedative effect.

18. A pharmaceutical formulation which comprises a flavonoid of formula (I) or a dimer thereof in admixture with a pharmaceutically acceptable carrier

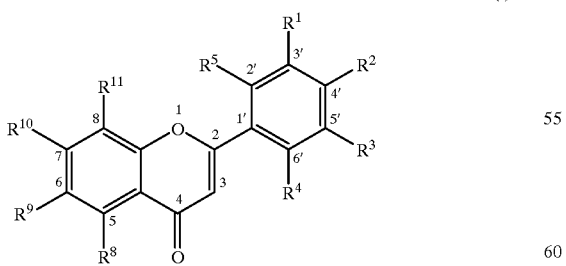

wherein $R^1$, $R^2$, $R^3$, $R^4$ are independently selected from $NO_2$ and H;

$R^8$, $R^{10}$ and $R^{11}$ are independently selected from H, —OH, —R, —$NO_2$, Br, Cl, F, —OR, —$NH_2$, —NHR, —$NR_2$, —COOR, —COOH, —CN or a sugar group;

$R^9$ is selected from H, $NO_2$, Br, Cl, or F;

R is $C_1$–$C_6$ alkyl or alkenyl;

with the proviso that at least one of $R^1$, $R^2$, $R^3$, $R^4$ and $R^5$ is $NO_2$ and with the exception that when $R^9$ is H, $R^5$ is H; or the administration of an effective non-toxic amount of bi-flavonoid which is a dimer of a compound of general formula (I).

19. A formulation according to claim 18 wherein $R^1$, $R^2$ and $R^5$ are independently selected from $NO_2$ and H;

$R^9$ is selected from H, $NO_2$, Br, Cl and F; with the proviso that at least one of $R^1$, $R^2$ and $R^5$ is $NO_2$ and with the exception that when $R^9$ is H, $R^5$ is H.

20. A formulation according to claim 18 wherein $R^1$, $R^2$ and $R^5$ are independently selected from H and $NO_2$;

$R^6$ and $R^7$ together form a single bond;

$R^9$ is selected from H, $NO_2$, Br, Cl and F; with the proviso that at least one of $R^1$, $R^2$ and $R^5$ is $NO_2$ and with the exception that when $R^9$ is H, $R^5$ is H.

21. A formulation according to claim 1 wherein $R^1$, $R^2$ and $R^5$ are independently selected from $NO_2$ and H;

$R^3$, $R^4$, $R^8$, $R^{10}$, and $R^{11}$ are all H;

$R^6$ and $R^7$ together form a single bond;

$R^9$ is selected from Br, Cl and F and $NO_2$;

with the proviso that at least one of $R^1$, $R^2$ and $R^5$ is $NO_2$.

22. A formulation according to claim 18 wherein the compound of general formula (I) is:

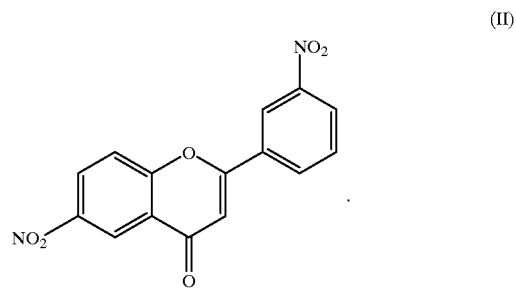

23. A formulation according to claim 18 wherein the compound of general formula (I) is:

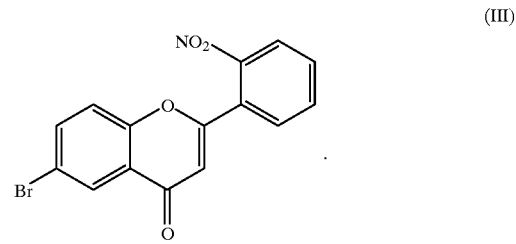

24. A formulation according to claim 18 wherein the compound of general formula (I) is:

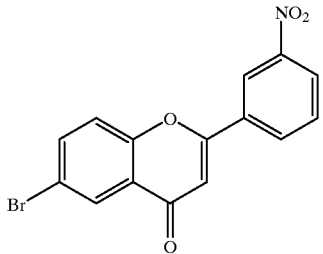
(IV)

25. A formulation according to claim 18 wherein the compound of general formula (I) is:

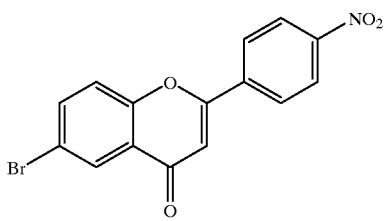
(V)

26. A formulation according to claim 18 wherein the compound of general formula (I) is:

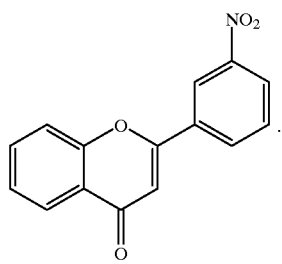
(VI)

27. A formulation according to claim 18 wherein the compound of general formula (I) is:

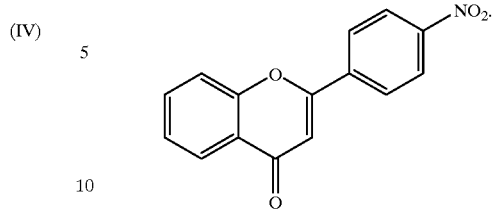
(VII)

28. A formulation according to claim 18 wherein the compound of general formula (I) is:

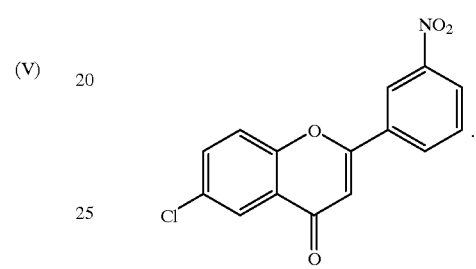
(VIII)

29. A formulation according to claim 18 wherein the compound of general formula (I) is:

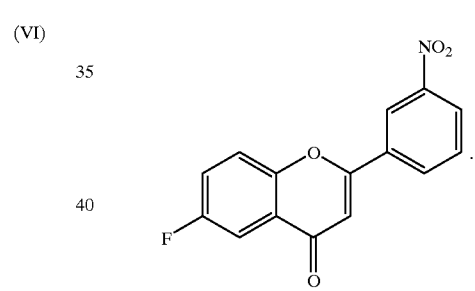
(IX)

30. A formulation according to claim 18 wherein the bi-flavonoid dimer is of general formula (X):

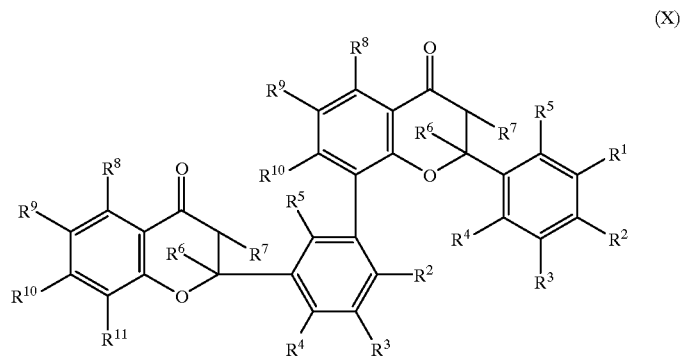
(X)

wherein $R^1$ to $R^{11}$ and R have the meaning given in claim 18.

31. A formulation according to claim 30 wherein at least one of $R^1$ and $R^2$ is $NO_2$;

$R^9$ is selected from H, Cl, Br, F and $NO_2$;

$R^6$ and $R^7$ are both H or $R^6$ and $R^7$ together form a single bond;

and all other R groups are hydrogen.

32. A formulation according to claim 30 wherein $R^1$ and $R^2$ are selected from H and $NO_2$;

$R^9$ is selected from $NO_2$, Br, F and Cl; and $R^6$ and $R^7$ are both H or $R^6$ and $R^7$ together form a single bond; and all other R groups are hydrogen.

33. A formulation according to claim 32 wherein the bi-flavonoid dimer is a dimer of monomers selected from compounds II, III, IV, V, VII, VIII, or IX.

34. A flavonoid compound of general formula (I):

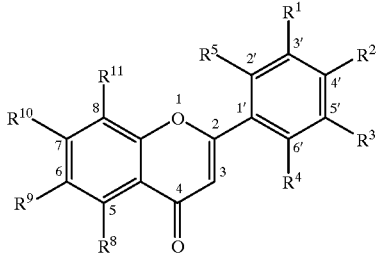

(I)

wherein $R^1$, $R^2$, $R^3$, $R^4$ and $R^5$ are independently selected from $NO_2$ and H;

$R^8$, $R^{10}$, and $R^{11}$ are independently selected from H, —OH, —R, —$NO_2$, Br, Cl, F, —OR, —$NH_2$, —NHR, —$NR_2$, —COOR, —COOH, —CN or a sugar group;

$R^9$ is selected from H, $NO_2$, Br, Cl, or F;

R is $C_1$–$C_6$ alkyl or alkenyl;

with the proviso that at least one of $R^1$, $R^2$, $R^3$, $R^4$ and $R^5$ is $NO_2$ and with the exception that when $R^9$ is H, $R^5$ is H; or a bi-flavonoid which is a dimer of a compound of general formula (I).

35. A compound according to claim 34 wherein $R^1$, $R^2$ and $R^5$ are independently selected from $NO_2$ and H;

$R^8$, $R^{10}$ and $R^{11}$ are all hydrogen;

$R^9$ is selected from H, $NO_2$, Br, Cl and F; with the proviso that at least one of $R^1$, $R^2$ and $R^5$ is $NO_2$ and with the exception that when $R^9$ is H, $R^5$ is H.

36. A compound according to claim 4 wherein $R^1$, $R^2$ and $R^5$ are independently selected from H and $NO_2$;

$R^6$ and $R^7$ together form a single bond;

$R^9$ is selected from H, $NO_2$, Br, Cl and F; with the proviso that at least one of $R^1$, $R^2$ and $R^5$ is $NO_2$ and with the exception that when $R^9$ is H, $R^5$ is H.

37. A compound according to claim 34 wherein:

$R^1$, $R^2$ and $R^5$ are independently selected from $NO_2$ and H;

$R^3$, $R^4$, $R^8$, $R^{10}$, and $R^{11}$ are all H;

$R^6$ and $R^7$ together form a single bond;

$R^9$ is selected from Br, Cl and F and $NO_2$;

with the proviso that at least one of $R^1$, $R^2$ and $R^5$ is $NO_2$.

38. A flavonoid compound according to claim 36 which is selected from compounds II, III, IV, V, VI, VII, VIII and IX.

39. A flavonoid compound according to claim 38 which is selected from compounds II, IV, VIII.

40. The compound:

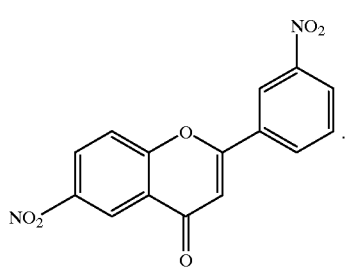

(II)

41. The compound:

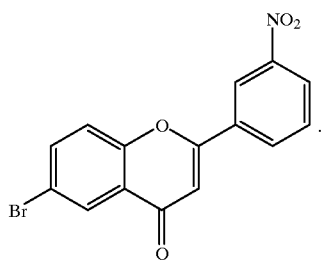

(IV)

42. The compound:

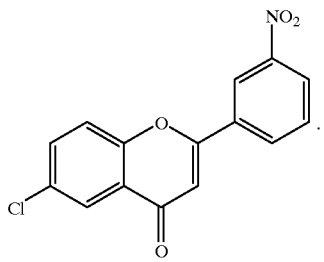

(VIII)

* * * * *

UNITED STATES PATENT AND TRADEMARK OFFICE
CERTIFICATE OF CORRECTION

PATENT NO.    : 6,080,780                              Page 1 of 2
DATED         : June 27, 2000
INVENTOR(S)   : Paladini et al.

It is certified that error appears in the above-identified patent and that said Letters Patent is hereby corrected as shown below:

Title page, Item [56] References Cited,
OTHER PUBLICATIONS, line 5, "mature" should read -- nature --;
Line 6, "B-flavanols" should read -- β-flavanols --;
Line 6, after "flavanols" insert -- and flavanones --;
Line 7, "Chemistry" should read -- Chemical --;
Line 8, "7-hydroxycromauones" should read -- 7-hydroxychromanones --.

Column 26,
Table 6, under the sub-heading "n", line 2, "2" should read -- 3 --.

Column 29,
Line 2, "or" should read -- and --.

Column 31,
Line 63, after $R^4$" insert -- and $R^5$ --.

Column 32,
Line 26, "claim 1" should read -- claim 18 --.

UNITED STATES PATENT AND TRADEMARK OFFICE
CERTIFICATE OF CORRECTION

PATENT NO. : 6,080,780
DATED : June 27, 2000
INVENTOR(S) : Paladini et al.

It is certified that error appears in the above-identified patent and that said Letters Patent is hereby corrected as shown below:

<u>Column 35,</u>
Line 17, after "V", insert -- VI, --;
Line 51, "claim 4" should read -- claim 34 --.

<u>Column 36,</u>
Line 12, after "IV", insert -- and --.

Signed and Sealed this

Fourteenth Day of August, 2001

*Attest:*

NICHOLAS P. GODICI
*Attesting Officer*  Acting Director of the United States Patent and Trademark Office